US007463927B1

(12) United States Patent
Chaouat

(10) Patent No.: US 7,463,927 B1
(45) Date of Patent: Dec. 9, 2008

(54) SELF-ADAPTIVE SYSTEM FOR THE AUTOMATIC DETECTION OF DISCOMFORT AND THE AUTOMATIC GENERATION OF SCS THERAPIES FOR CHRONIC PAIN CONTROL

(75) Inventor: Laurent Francois Chaouat, Austin, TX (US)

(73) Assignee: Intelligent Neurostimulation Microsystems, LLC, Austin, TX (US)

( * ) Notice: Subject to any disclaimer, the term of this patent is extended or adjusted under 35 U.S.C. 154(b) by 236 days.

(21) Appl. No.: 11/218,192

(22) Filed: Sep. 1, 2005

Related U.S. Application Data

(60) Provisional application No. 60/606,726, filed on Sep. 2, 2004.

(51) Int. Cl.
*A61N 1/34* (2006.01)
(52) U.S. Cl. .......................................... 607/46
(58) Field of Classification Search ............ 607/46, 607/117
See application file for complete search history.

(56) References Cited

U.S. PATENT DOCUMENTS

| | | | |
|---|---|---|---|
| 4,233,986 A | 11/1980 | Tannenbaum | |
| 4,690,142 A | 9/1987 | Ross et al. | |
| 4,735,204 A | 4/1988 | Sussman et al. | |
| 4,738,250 A | 4/1988 | Fulkerson et al. | |
| 5,257,623 A | 11/1993 | Karasev et al. | |
| 5,291,883 A | 3/1994 | Kreutner | |
| 5,449,378 A | 9/1995 | Schouenborg | |
| 5,496,354 A | 3/1996 | De Bellis | |
| 5,649,967 A | 7/1997 | De Bellis et al. | |
| 5,674,262 A | 10/1997 | Tumey | |
| 5,702,426 A | 12/1997 | Pons et al. | |
| 5,702,428 A | 12/1997 | Tippey et al. | |
| 5,724,996 A | 3/1998 | Piunti | |
| 5,735,887 A | 4/1998 | Barreras, Sr. et al. | |
| 5,752,978 A | 5/1998 | Chancellor | |
| 5,792,187 A | 8/1998 | Adams | |
| 5,797,966 A | 8/1998 | Bontoux et al. | |
| 5,895,416 A | 4/1999 | Barreras, Sr. et al. | |
| 5,913,882 A | 6/1999 | King | |
| 5,922,016 A | 7/1999 | Wagner | |

(Continued)

OTHER PUBLICATIONS

Tulgar, M., "New Approaches to Electrical Stimulation of the Nervous System for the Relief of Pain." PhD Thesis, University of Liverpool, 1991, Chapter 4.

(Continued)

*Primary Examiner*—Carl H. Layno
*Assistant Examiner*—Brian T Gedeon
(74) *Attorney, Agent, or Firm*—Pearl Cohen Zedek Latzer, LLP

(57) ABSTRACT

A system for treating pain consisting of an "add-on" module integrated within the implantable pulse generator (IPG) component of IPG spinal cord stimulators, or, alternatively, integrated within the radiofrequency (RF) transmitter component of RF spinal cord stimulators. The system automatically and continuously monitors, measures, and classifies multiple patient physiological parameters without human intervention. The system also classifies qualitative perceptive changes felt by the patient. On the basis of this input vector information, the system automatically and continuously generates the most appropriate stimulation programs to improve, alleviate, or eliminate the patient's pain without human intervention. The system automatically and continuously adapts itself to both quantitative physiological changes within the patient and qualitative perceptive changes felt by the patient.

18 Claims, 11 Drawing Sheets

System Context Overview

U.S. PATENT DOCUMENTS

| | | | |
|---|---|---|---|
| 6,349,233 B1 | 2/2002 | Adams | |
| 6,445,955 B1 | 9/2002 | Michelson et al. | |
| 6,622,048 B1 | 9/2003 | Mann et al. | |
| 6,711,442 B1 | 3/2004 | Swerdlow et al. | |
| 6,871,099 B1 * | 3/2005 | Whitehurst et al. | 607/46 |
| 6,909,917 B2 | 6/2005 | Woods et al. | |
| 7,142,927 B2 * | 11/2006 | Benser et al. | 607/63 |
| 7,206,632 B2 * | 4/2007 | King | 600/544 |
| 7,266,412 B2 * | 9/2007 | Stypulkowski | 607/48 |
| 2002/0193844 A1 | 12/2002 | Michelson et al. | |
| 2003/0144709 A1 | 7/2003 | Zabara et al. | |
| 2003/0153959 A1 | 8/2003 | Thacker et al. | |
| 2004/0116978 A1 | 6/2004 | Miller | |

OTHER PUBLICATIONS

Barolat, Giancarlo, "Current Status of Epidural Spinal Cord Stimulation," Neurosurgery Quarterly 5(2), pp. 98-124, Raven Press, New York.

Barolat, Giancarlo, et. al. "Multifactoral Analysis of Epidural Spinal Cord Stimulation," Stereotact Funct Neurosurg, vol. 56, pp. 77-103, 1991.

Holsheimer, et. al, "Optimum Electrode Geometry for Spinal Cord Stimulation," Medical & Biological Engineering & Computing, Jul. 1997.

Barolat G., Massaro F., He J., Zeme S., Ketcik B., "Mapping of Sensory Responses to Epidural stimulation of the Intraspinal Neural Structures", in man. J Neurosurg 1993, 78:233-239.

North RB., Ewend MG., Lawton MT., Piantadosi S., "Spinal Cord Stimulation for Chronic Intractable Pain: Superiority of Multichannel Devices", Pain 1991; 44:119-130.

Long DM., Erickson D., "Stimulation of the Posterior Columns of the Spinal Cord for Relief of Intractable Pain", Surg Neurol 1975; 4:134-141.

Meglio M., Cioni B., Rossi GF., "Spinal Cord Stimulation in Management of Chronic Pain", J Neurosurg 1989; 70:519-524.

Augustinsson LE., Carlsson CA., Holm J., Jivegard L., "Epidural Electrical Stimulation in Severe Limb Ischemia", Ann Surg 1985; 202:104-110.

Jacobs MJ., Jorning PJ., Beckers RC., Ubbink DT., Van Kleef M., Slaaf DW., Reneman RS., "Foot Salvage and Improvement of Microvascular Blood Flow as a Result of Epidural Spinal Cord Eectrical Stimulation", J Vasc Surg 1990; 12:354-360.

Dimitrijevic M., "Neurophysiological Evaluation and Epidural Stimulation in Chronic Spinal Cord Injury Patients", in Kao CC., Bunge RP., Reier PJ (eds): *Spinal Cord Reconstruction*. New York, Raven Press, 1983, pp. 465-474.

Barolat G., Myklebust JB., Hemmy DC., Wenninger W., "Immediate Effects of Spinal Cord Stimulation in Spinal Cord Stimulation in Spinal Spasticity", J Neurosurg 1985; 62:558-562.

Dimitrijevic MR., Faganel J., Young RR., "Underlying Mechanisms of the Effects of Spinal Cord Stimulation in Motor Disorders", Appl Neurophysiol 1981; 44:133-140.

Bantli H., Bloedel JR., Long DM., Thienprasit P., "Distribution of Activity in Spinal Pathways Evoked by Experimental Dorsal Column Stimulation", J Neurosurg 1975; 42:290-294.

Phillips CG., "Possible Modes of Action of Extradural Electrical Stimulation on the Spinal Cord", Appl Neurophysiol 1981; 44:16-21.

Gybels J., Van Roost D., "Spinal Cord Stimulation for the Modification of Dystonic and Hyperkinetic Conditions: A critical review", in Eccles J., Dimitrijevic MR (eds): *Recent Achievments in Restorative Neurology. I. Upper Motor Neuron Functions and Dysfunctions*, Basel, Karger, 1985, pp. 56-70.

Swiontek TJ., Sances A., Larson SJ., et. al., "Spinal Cord Implant Studies", IEEE Trans. Biomed Eng. 1976, BME-23: 307-312.

Coburn B., "Electrical Stimulation of the Spinal Cord: Two-Dimensional Finite Element Analysis with Particular Reference to Epidural Electrodes", Med Biol Eng Comp 1980, 18:573-584.

Sin WK., Coburn B., "Electrical Stimulation of the Spinal Cord: A Further Analysis Relating to Anatomical Factors and Tissue Properties", Med Biol Eng Comp 1983; 21:264-269.

Coburn B., Sin WK., "A Theoretical Study of Epidural Electrical Stimulation of the Spinal Cord. Part I. Finite Element Analysis of Stimulus Fields", IEEE Trans Biomed Eng 1985; BME-32:971-977.

Coburn B., "A Theoretical Study of Epidural Electrical Stimulation of the Spinal Cord. Part II. Effects on Long Myelinated Fibers", IEEE Trans Biomed Eng 1985; BME-32:978-986.

Holsheimer J., Struijk JJ., "Electrode Combination and Specificity in Spinal Cord Stimulation", Proc 9$^{th}$ Int Symp Advances in External Control of Human Extremities, Dubrovnik, 1987, pp. 393-404.

Holsheimer J., Struijk JJ., "Analysis of Spinal Cord Stimulation. I. Field Potentials Calculated for a Homogeneous Medium" in Wallinga W., Boom HBK., de Vries J. (eds): *Electrophysiological Kinesilogy*, Amsterdam, excerpta Medica Congress Series, 1988, vol. 804, pp. 95-98.

Struijk JJ., Holsheimer J., Van Veen BK., et. al., "Analysis of Spinal Cord Stimulation. II. Simulation of Field Potentials in an Inhomogeneous Medium", in Wallinga W., Boom HBK., de Vries J. (eds): *Electrophysiological Kinesiology*, Amesterdam, Excerpta Medica Congress Series, 1988, vol. 804, pp. 99-102.

Holsheimer J., Struijk JJ, "Improvement of Methods in Spinal Cord Stimulation", Int J Rehab Res 1989, 11:409-410.

Struijk JJ., Holsheimer J., Van Veen BK., Boom HBK., "Epidural Spinal Cord Stimulation: Calculation of Field Potentials with Special Reference to Dorsal Column Nerve Fibers", IEEE Trans Biomed Eng 1991; BME-38:104-110.

T. Kohonen, "Self-Organization and Associative Memory" Springer-Verlag, 1984, ISBN: 3-540-12165-X. Third edition 1989, pp. 30-89, 189-209.

L. Davis, "Handbook of Genetic Algorithms" Van Nostrand Reinhold, 1991. pp. 1-22.

North RB, Nigrin DJ, Fowler KR, et al: Automated Pain Drawing analysis by computer-controlled, patient-interactive neurological stimulation system. Pain 50:51-57, 1992.

Tulgar Metin "New Approaches to Electrical Stimulation of the Nervous System for the Relief of Pain" PhD thesis, University of Liverpool, 1991, chap. 4.

* cited by examiner

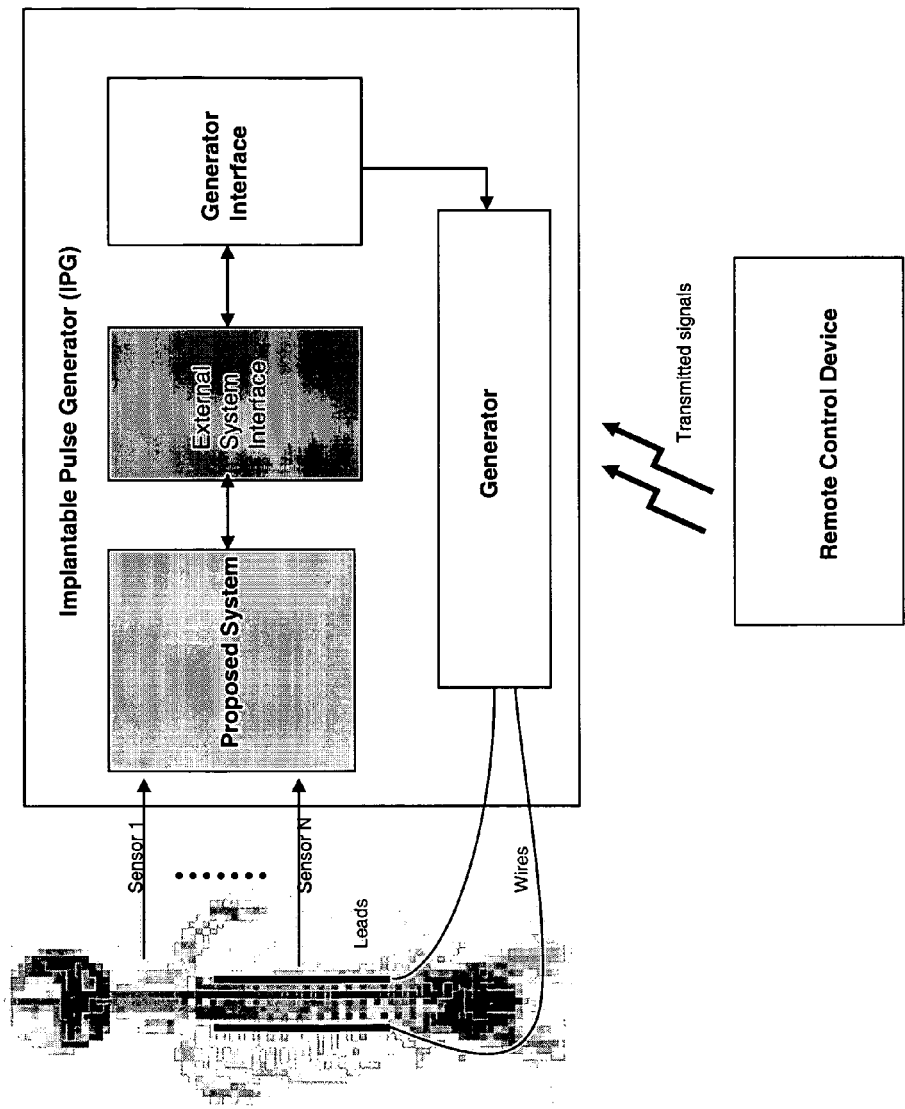
Figure 1: System Context Overview

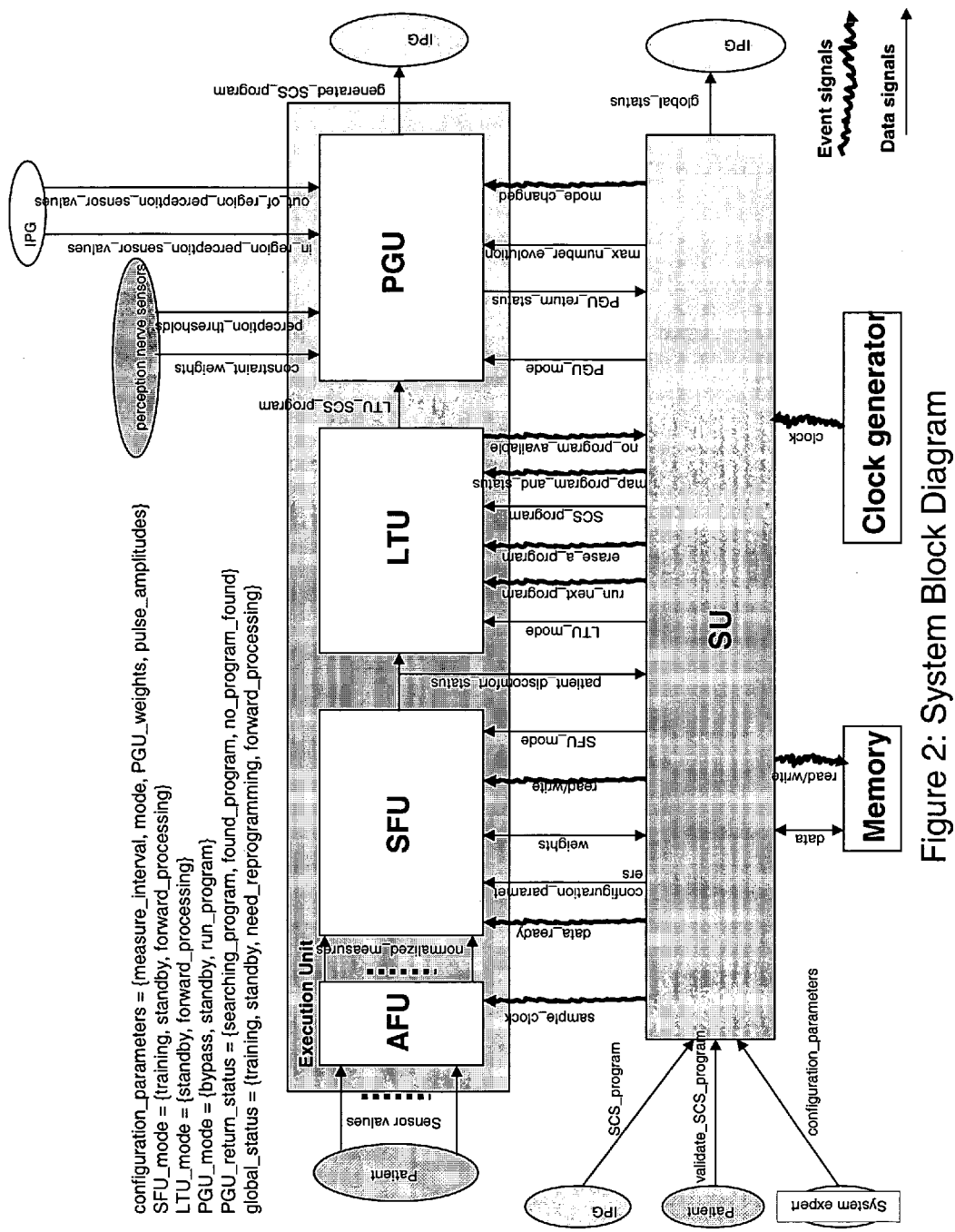
Figure 2: System Block Diagram

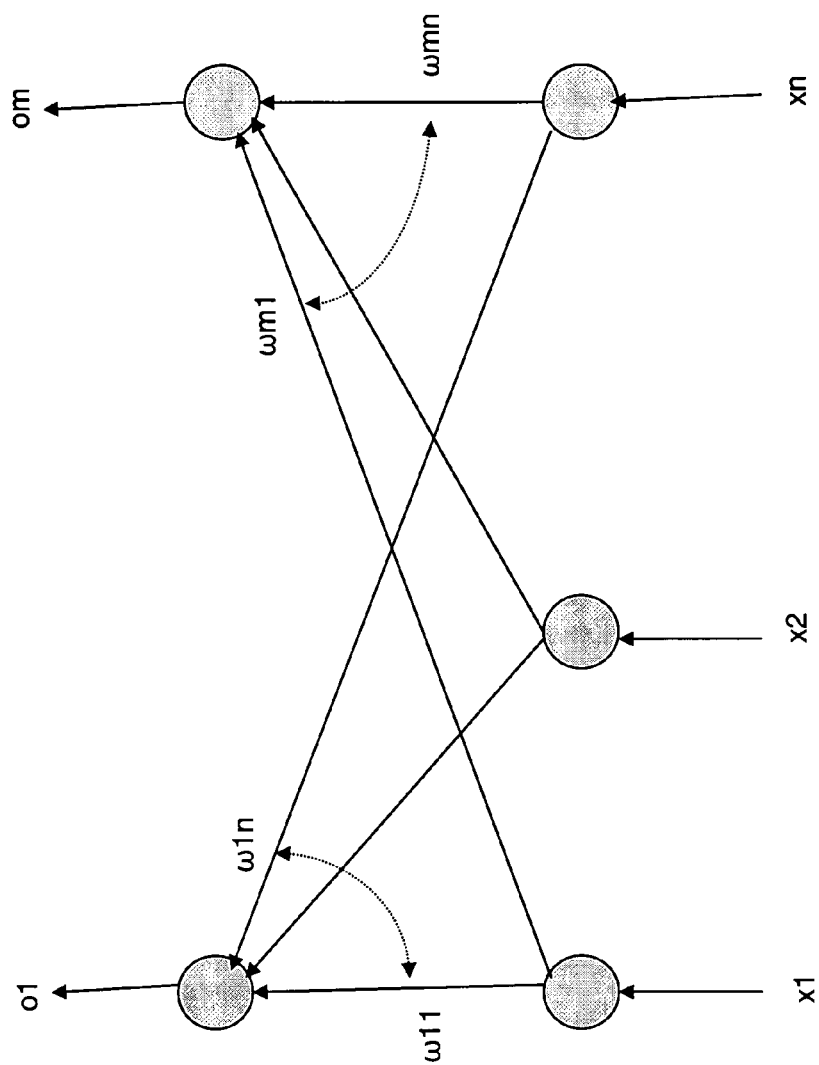
Figure 3: The Kohonen Neural Network

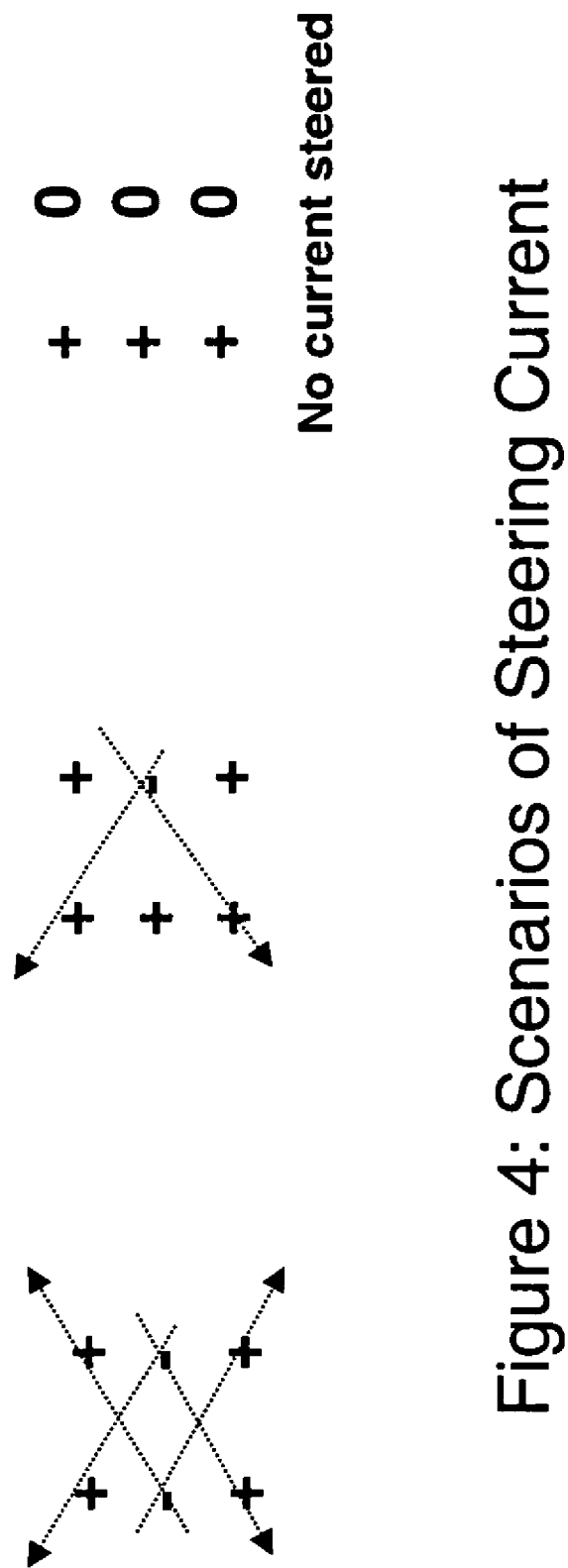

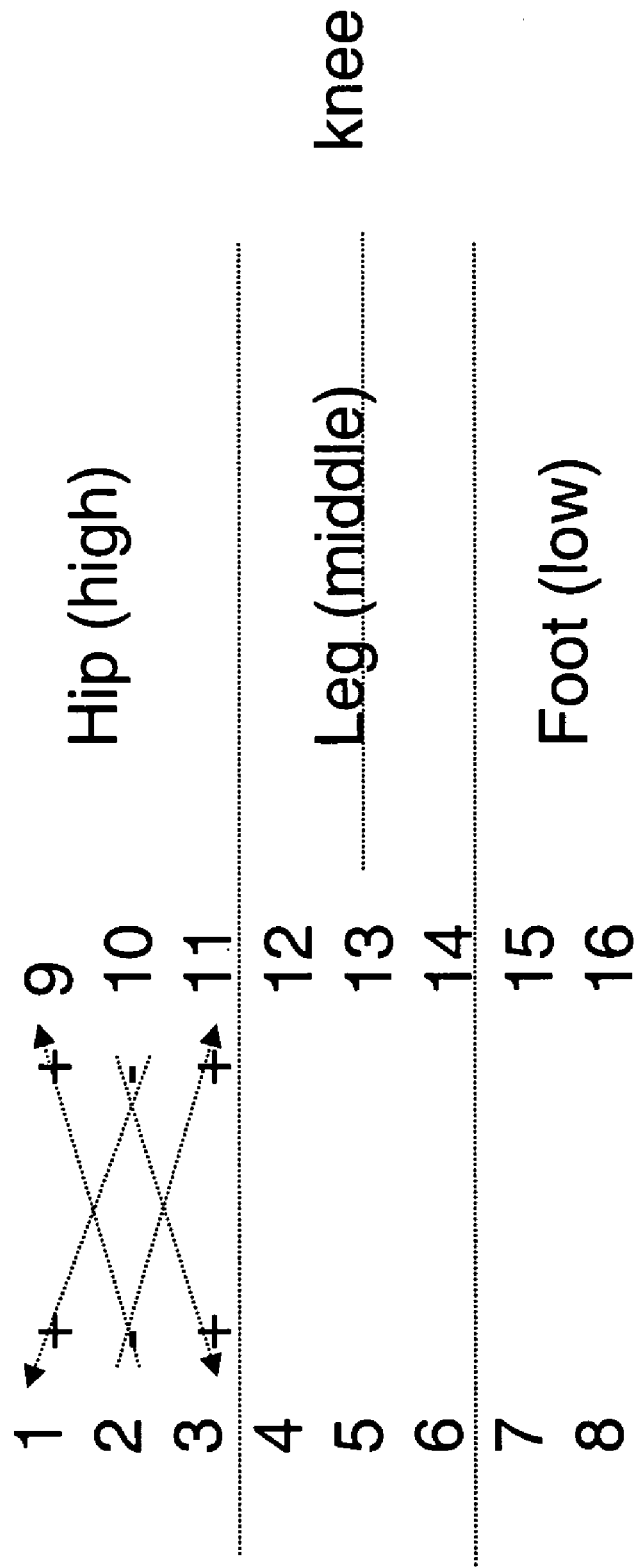
Figure 5: Lead Placement Scenario

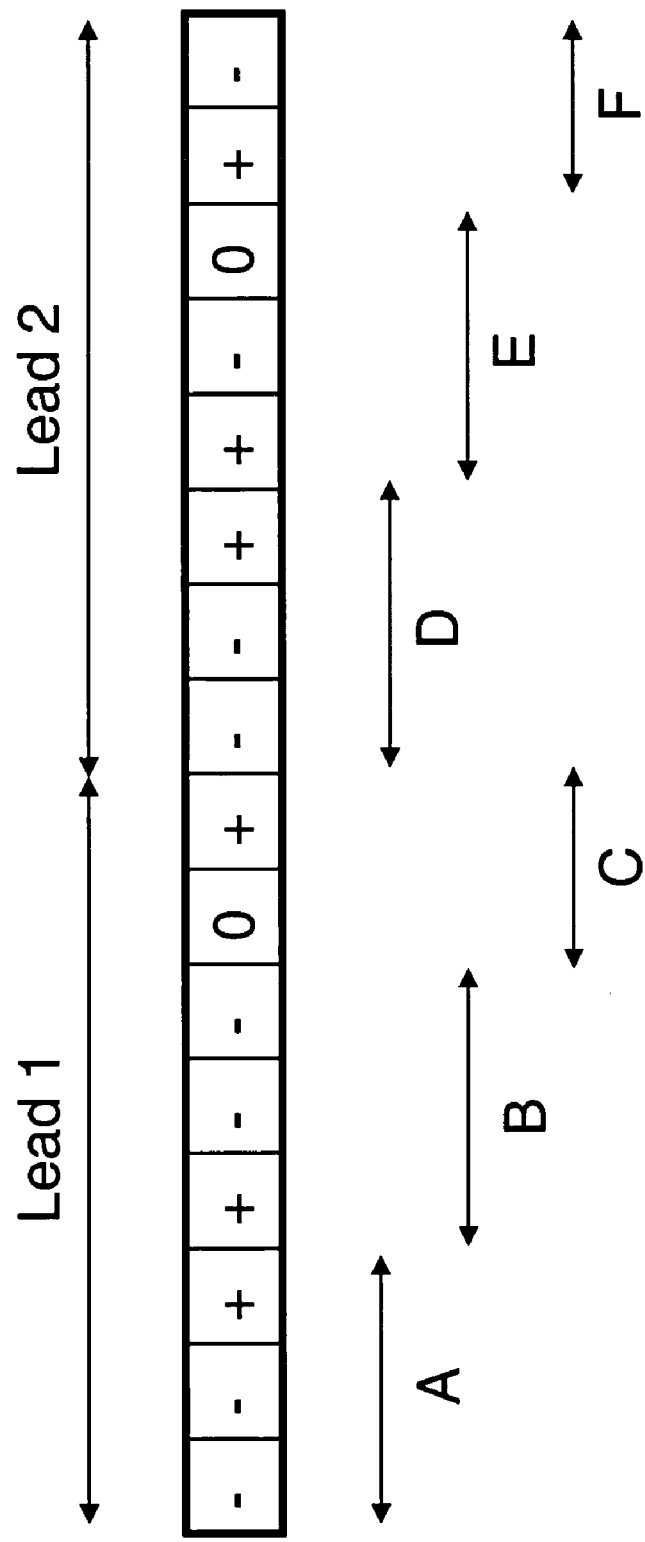
Figure 6: Chromosome Representation

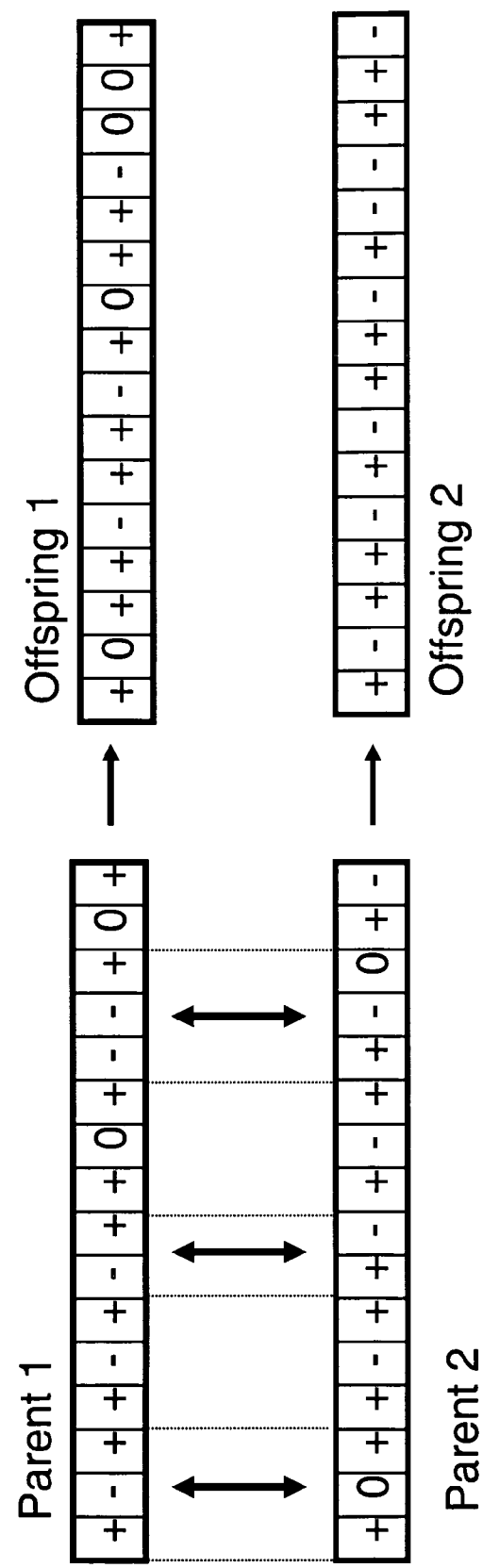
Figure 7: Crossover Example

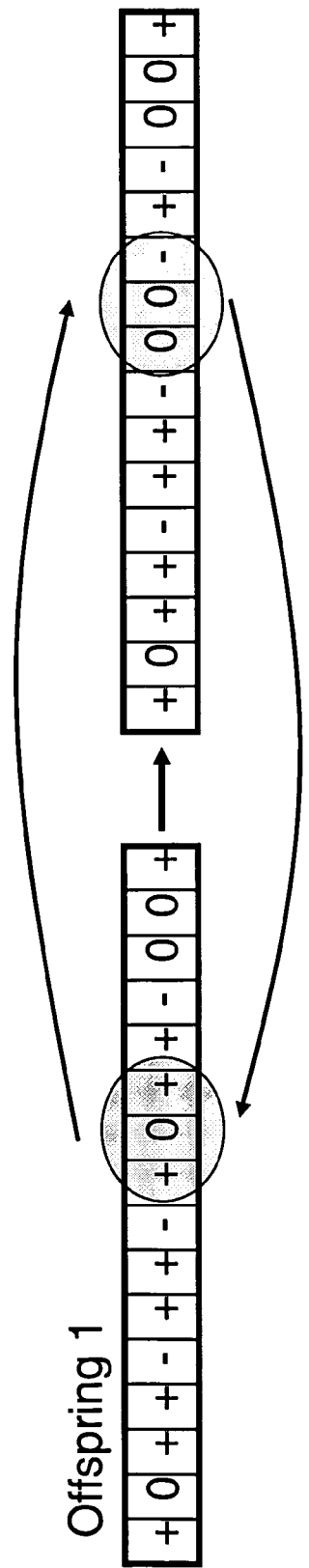
Figure 8: Mutation Example

+ + + o o o o + o

+ + +

ı ı ı

ı ı ı

+ + +

+ + +

Figure 9: Examples of Undesired Combinations

1. [Initialization] Create initial population of chromosomes composed of programs stored in the LTU and randomly generated chromosomes from the gene pool.
2. [Fitness] Determine the fitness of each chromosome that makes up the population.
3. [Evolution] Create new offspring population by repeating the following steps:
    3.1 [Selection] Base on their fitness, and the selection procedure ("tournament selection"), pick two parent chromosomes.
    3.2 [Crossover] Crossover the selected parent chromosomes according to the defined crossover probability to form new offspring chromosomes.
    3.3 [Mutation] Randomly mutate some of the genes of the new offspring chromosomes based on the mutation probability. Place new chromosomes in the population.
4. [Test] Test best solutions on patient, and stop if end criteria satisfied.
5. [Repeat] Repeat step 2 if stop condition not satisfied.

Figure 10: Genetic Algorithm for the Automatic SCS program Generation

Figure 11: Gene Pool

SELF-ADAPTIVE SYSTEM FOR THE AUTOMATIC DETECTION OF DISCOMFORT AND THE AUTOMATIC GENERATION OF SCS THERAPIES FOR CHRONIC PAIN CONTROL

CROSS-REFERENCE TO RELATED APPLICATIONS

This application claims the benefit of provisional patent application Ser. No. 60/606,726, filed 2004 Sep. 2 by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention relates to spinal cord stimulation (SCS) devices, specifically to a component system which, when "added on" to existing (or future) SCS devices, will greatly enhance these SCS devices by automatically monitoring, measuring, and classifying a patient's levels of discomfort, automatically generating the most appropriate "programs" or "therapies" to relieve the patient's pain, and automatically self-adapting itself to changes within the patient over time.

2. Prior Art

More than 20 years ago, electrical stimulation of the spinal cord or "dorsal column stimulation" was introduced in the treatment of chronic pain. This approach is called spinal cord stimulation (SCS). SCS works by blocking pain signals from being received by the brain through the surgical insertion of electrodes along different points of the spinal cord. SCS therapies use precise, low-voltage electrical stimulation through one or two carefully placed insulated leads in the spinal cord. Trial-and-error is used to find the optimal combination of signals in a program that would eliminate or at least mitigate the pain.

Since my invention will serve as an add-on to existing (or future) implantable devices that target the spinal cord stimulation pain market, I offer a comprehensive overview of existing device technology and components.

A spinal cord stimulation system uses several components for relieving chronic, intractable pain in the cervical area, the trunk and/or limbs, and the legs and/or feet. It applies precisely controlled low-voltage electrical stimulation to the spinal cord through one or two carefully placed insulated leads. The surgical procedure involves the insertion of a compact implantable pulse generator (IPG) in the lower anterior abdomen wall that is connected to a strip of electrodes implanted adjacent to the back part of the spinal cord. The leads are implanted near the spinal nerves that correspond to the patient's pain areas. Through low-voltage electrical stimulation of these electrodes, the normal pain signals that travel in the posterior part of the spinal cord are blocked, providing partial or complete pain relief.

Apart from the electrodes, the system includes an implantable pulse generator in an area agreed to by the patient, and an external remote device worn on the patient's belt. The remote control device sends signals to the implantable pulse generator, stimulating the spinal cord via the leads. In this way, messages of pain are prevented from reaching the thalamus in the brain. As a result, the patient feels a "tingling" sensation called paraesthesia, instead of pain.

A spinal cord stimulator (SCS) system for pain relief contains a remote control device programmed by a small computer, an antenna, an implantable pulse generator, and epidural multi-electrode leads which offer a better choice of stimulation combinations. The implantable pulse generator and the epidural electrodes are connected through subcutaneous lead wires.

The implantable pulse generator is surgically implanted, usually in the patient's abdominal area and tunneled under the skin to connect the leads and extensions, such as the wires. The implantable pulse generator receives electrical pulses from the remote control device and sends them to the spinal cord or, in some cases, to a peripheral nerve to control the patient's pain. The implantable pulse generator has permanently attached extensions that connect to the leads. It is a pulse generator that delivers adjustable signals. One can tune 3 different parameters: Pulse width (from 10 to 500 micro seconds), Frequency (10 to 1500 Hz), and Amplitude (0.1V to 12.0V). Typically, the starting pulse width parameter is between 150 and 500 microseconds for pain located in the thoracic area, and between 50 and 250 microseconds for pain located in the cervical area. The amplitude should always be kept as low as possible in order to preserve battery life.

Each lead is implanted in the epidural space next to the spinal cord at a spot that corresponds to the patient's pain (between the C2 and L1 vertebra levels). They are placed so that the patient feels "tingling" instead of pain in the part(s) of the body being stimulated. The electrodes at the tip of each lead carry the electrical impulses to the spinal nerves, creating a tingling feeling rather than the sensation of pain.

A lead consists of one or more contacts encased in one implanted structure. A contact or electrode is the basic stimulation component that represents one of the poles of the current flow. A lead is typically around a 1.5 to 2 mm diameter catheter 60 cm long. Each lead contains 4 to 8 controllable contacts. Since electrical current flows between a positive pole and a negative pole, there must be at least one anode and one cathode electrode in order to cause any stimulation. Sometimes a positive electrical stimulation is needed, and sometimes a negative stimulation is better. Not all electrodes need to be active. Thus, there is an additional polarity "state" termed "off" (the electrode polarity is zero (0)). With this amount of electrodes, the number of possible electrode polarity combinations (3 per electrode negative, positive and neutral) can reach $3^{16}$, which equals 43,046,721 (for 16 electrodes—8 electrodes on each lead). Once the physician defines exactly what areas of the body needs treatment, he or she has to set the optimal stimulation settings by determining the best polarity combinations. This is very difficult to achieve. The only way to accomplish this is through experimentation and previous physician expertise.

The programming information for the SCS system are provided by and downloaded from an external remote device. The clinician uses this remote control device to set stimulation parameters. The remote control device produces a signal that sends programs that are transmitted through the skin via an attached antenna positioned over the implantable pulse generator. A major advantage of this system is that the remote control device can be customized through a computer driven interface.

The stimulation parameters (electrical signal parameters, and contact polarity), as well as the leads placement, are set and adjusted through hardware/software programming consoles. The hardware consists of a portable computer that can be connected to the remote control device.

It is important to note that spinal cord stimulator (SCS) devices and other implantable tissue stimulator systems come in two general types: radiofrequency (RF) controlled and fully implanted like the implantable pulse generator (IPG)—based devices described above.

The fully implanted (IPG) type of stimulating system contains the programmable stimulation information in memory, as well as a power supply, e.g., a battery, all within the implanted pulse generator, or "implant", so that once programmed and turned on, the implant can operate independently of external hardware. The implant is turned on and off and programmed to generate the desired stimulation pulses from an external programming device using transcutaneous electromagnetic, or RF links. Such stimulation parameters include, e.g., the pulse width, pulse amplitude, repetition rate, and burst rates.

The second type of stimulating system, commonly referred to as an "RF" system, includes an external transmitter inductively coupled via an electromagnetic link to an implanted receiver that is connected to a lead with one or more electrodes for stimulating the tissue. The power source, e.g., a battery, for powering the implanted receiver-stimulator as well as the control circuitry to command the implant is maintained in the external unit, a hand-held sized device that is typically worn on the patient's belt or carried in a pocket. The data/power signals are transcutaneously coupled from a cable-connected transmission coil placed over the implanted receiver-stimulator device. The implanted receiver-stimulator device receives the signal and generates the stimulation. The external device usually has some patient control over selected stimulating parameters, and can be programmed from a physician programming system.

My invention is not limited to working with implantable pulse generator based spinal cord stimulators. It also works perfectly with radiofrequency (RF) based spinal cord stimulators. The advantage of radiofrequency type SCS devices is that the battery can be easily changed or recharged. Previously, radiofrequency SCS systems would have been better suited for patients with more complicated pain patterns, which require more energy and programming. However, the development of rechargeable batteries for implantable pulse generator SCS systems very recently means that implantable pulse generator SCS systems are not at a disadvantage in this regard any longer.

Programs are generally composed of different modules that address all the various aspects of SCS, including patient management, billing, patient testing, and analysis of the implanted stimulator and the stimulation patterns. Based on information provided by the patient on the pain characteristics and patterns, the software makes suggestions as to the optimal electrode placement. The patient enters this information through a graphical interface by drawing the pain area on the screen (map of the body) using a pen. The pain intensity and the critical areas are also given. Once the electrodes are implanted, the program can be downloaded into the radio receiver and the electrical parameters can be modified. The information obtained through a patient-interactive module is then recorded in a database.

Current SCS device technology is outdated, unintelligent, inconvenient, and inefficient. Patient program settings are based on "trial and error" approaches and patient "hunches." Setting, programming, and tuning SCS devices is largely manual, and is very time consuming for physicians and patients alike. Current SCS devices cannot adjust stimulation based upon real-time patient physiological parameters and changes. The only way SCS programs can be updated/changed is by a physician's intervention.

The main drawback of such existing systems is that they do not contain any intelligence or facility to determine the most appropriate electrode combinations (contact polarization) and electrical parameters. This is currently done manually through a tedious and non-deterministic interactive process with the patient. A few days after surgery, the physician will provide the patient with a set of programs loaded in the implantable pulse generator. These programs (position of the contacts and parameters of the electrical signal) are determined from the patient oral feedbacks. The patient then returns home and evaluates them for several weeks in order to give the physician some additional feedback. Then, during subsequent follow-up visits, the physician will erase some programs, and slightly modify others to provide the most appropriate settings for the patient. The whole procedure is very long, and very costly.

One of the key factors for successful electrical stimulation therapy is the accurate settings of electrical parameters.[1] The optimal parameters are based on the evaluation of three physiological variables elicited by electrical stimulation of the intra-spinal structures: the paraesthesia response, the perception intensity and the usage range.

[1] Barolat G., Zeme S., Ketcik B., "Multifactorial analysis of epidural spinal cord stimulation", Stereotact Funct Neurosurg 1991; 56:77-103.

It is essential for the patient to experience paraesthesia, a pleasant tingling sensation in the painful area during the stimulation. In clinical applications, electrical stimulation starts with the lowest intensity of current (ideally with 0 mA), and it is then gradually increased until the patient feels a slight tingling.

The first response by the patient is called "stimulation perception threshold". After the determination of the perception threshold, the intensity is slowly increased again. When the maximal bearable level of stimulation is reached, the patient may feel painful muscle contractions. This level of intensity corresponds to the "tolerance threshold". The patient tolerance is critical, particularly if unpleasant sensations are felt just over the perception threshold or if they occur before sufficient intensity has been reached to achieve paraesthesia.

Adjustable electrical parameters, including amplitude, pulse width, frequency, polarity (contact configuration), and pulse modulation, are available in the clinically used SCS devices.[2] There are many publications in the present literature reporting the clinical results of SCS therapy applications.[3] However, only a few published studies involving the systematic analysis of perception intensities have focused on the optimal parameters to achieve successful spinal cord stimulation.[4] Research studies revealed that the output of a spinal cord stimulator must not exceed 10V (10 mA), and the majority (70%) required treatment levels of less than 5V (5 mA). No previous study has addressed the question of how electrode location and contact configuration affect the perception intensity of stimulation.

[2] Barolat G., Massaro F., He J., Zeme S., Ketcik B., "Mapping of sensory responses to epidural stimulation of the intraspinal neural structures", in man. J neurosurg 1993, 78:233-239. North RB., Ewend M G., Lawton M T., Piantadosi S., "Spinal cord stimulation for chronic intractable pain: Superiority of multichannel devices", Pain 1991; 44:119-130. North R B., Ewend M G., Lawton M T., Piantadosi S., "Spinal cord stimulation for chronic intractable pain: Superiority of multichannel devices", Pain 1991; 44:119-130.
[3] Long D M., Erickson D., "Stimulation of the posterior columns of the spinal cord for relief of intractable pain", Surg Neurol 1975; 4:134-142. Meglio M., Cioni B., Rossi G F., "Spinal cord stimulation in management of chronic pain", J Neurosurg 1989; 70:519-524. Augustinsson L E., Carlsson C A., Holm J., Jivegard L., "Epidural electrical stimulation in severe limb ischemia", Ann Surg 1985; 202:104-110. Jacobs M J., Jorning P J., Beckers R C., Ubbink D T., Van Kleef M., Slaaf D W., Reneman R S., "Foot salvage and improvement of microvascular blood flow as a result of epidural spinal cord electrical stimulation", J Vasc Surg 1990; 12:354-360. Dimitrijevic M., "Neurophysiological evaluation and epidural stimulation in chronic spinal cord injury patients", in Kao C C., Bunge R P., Reier P J (eds): Spinal Cord Reconstruction. New York, Raven Press, 1983, pp. 465-474. Barolat G., Myklebust J B., Hemmy D C., Wenninger W., "Immediate effects of spinal cord stimulation in spinal cord stimulation in spinal spasticity", J Neurosurg 1985; 62:558-562.
[4] Tulgar M., *New Approaches to Electrical Stimulation of the Nervous System for the Relief of Pain*; PhD thesis, University of Liverpool, 1991, chap. 4. Fluks J., Lindemans F W., "Medtronic Itrel Totally Implantable Stimulation System", Kerkrade, Medtronic BV International Research and Science Centre, 1984.

The configuration process consists of: (a) optimizing the placement of the leads; and (b) finding the right values for the electrical stimulation parameters (programs) to enhance the possibility of obtaining a result that will cover as completely as possible the painful area(s) of the body. At first, the leads must be surgically inserted somewhere along the spinal cord depending on the pain location. Some rules or guidelines[5] have been defined as to where approximately one should place the electrodes. The resulting implants often do not lead to exactly the points that are connected with the targeted pain locations. Thus, these locations often need some adjustment based on the patient's reaction. It could be very useful to use a database that contains the experience of successful lead placements in order to automate this task. For the purposes of this invention, however, we will only focus on the second stage: SCS parameter selection and automatic control.

[5] Giancarlo Barolat, "Current Status of Epidural Spinal Cord Stimulation", Neurosurgery quarterly 5(2), pp. 98-124, Raven press Ltd., New York, 1995. Giancarlo Barolat, et. al., "Multifactorial Analysis of Epidural Spinal Cord Stimulation", Stereotact Funct Neurosurg, Vol. 56, pp. 77-103, 1991. J. Holsheimer, et. al., "Optimum electrode geometry for spinal cord stimulation: the narrow bipole and tripole", Medical & Biological Engineering & Computing, July 1997.

The settings for all stimulation parameters (contact polarities, frequency, pulse width, amplitude, and contact currents) result in a program that is loaded in the remote control device's memory in order to be transmitted to the implantable pulse generator. The selection of electrode polarities (+, −, 0) is used to "target" a specific pain site. For that specific task, there is some preliminary knowledge that describes what exact polarity combinations and frequency one needs to select to enhance the coverage of the area affected by the pain. For example, in the case of a low-back pain, the leads are usually inserted between areas T8 and T10 of the spinal cord (covered areas are hips, legs, and feet). If one sends a + signal to point No. 1,− signal to point No. 2, and + signal to point No. 3, and no signals to all other points, then this combination of polarities described by the sequence +−+00000 may in most cases result in relief to the hips of the patient. If the pain is caused by motor neurons, one requires a frequency of about 1 Hz; to target pain on other neurons, one needs larger frequencies (~10-20 Hz).

This is the preliminary knowledge required to generate the first (draft) program. After that, the physician must determine the amplitude. He starts with the smallest possible amplitude that is most probably not perceived by the patient, and increases the amplitude until the patient starts feeling the effect (the "tingling"). The patient must also indicate in which of the zones he has this feeling. If some of these feelings are in undesired zones, some parameters of the programs must be adjusted according to the patient's feedback. If all the feelings are in the desired zones, one may begin increasing the amplitude until the level when the feeling becomes uncomfortable is obtained. For a given program, these two thresholds are marked down, and in the future, amplitudes of using this program must be between these two values.

The primary reasons for this relatively primitive methodology for configuring SCS programs are:

a) a lack of systematic research on the relationship between stimulus and electrode parameters and their clinical effects;

b) insufficient knowledge regarding both the neuronal elements in the spinal cord that are actually stimulated and the elements that have to be stimulated in order to obtain an adequate clinical effect.[6]

c) And, most importantly, prior to my invention, a complete lack of the required technology advanced enough to allow SCS devices to operate in an automatic, self-adaptive manner.

[6] Dimitrijevic M R, Faganel J., Young RR., "Underlying mechanisms of the effects of spinal cord stimulation in motor disorders", Appl Neurophysiol 1981; 44:133-140. Bantli H., Bloedel J R., Long D M., Thienprasit P., "Distribution of activity in spinal pathways evoked by experimental dorsal column stimulation", J Neurosurg 1975; 42:290-295. Phillips C G., "Possible modes of action of extradural electrical stimulation on the spinal cord", Appl Neurophysiol 1981; 44:16-21. Gybels J., Van Roost D., "Spinal cord stimulation for the modification of dystonic and hyperkinetic conditions: A critical review", in Eccles J., Dimitrijevic M R (eds): *Recent Achievements in Restorative Neurology. I. Upper Motor Neuron Functions and Dysfunctions*, Basel, Karger, 1985, pp. 56-70.

Some investigations have focused on the neural target elements of SCS. Swiontek et al.[7] measured stimulus induced potential distributions in cadaver spinal cords. A theoretical investigation considering the targets of stimulation was initiated by the late Barry Coburn.[8] In these studies, a computer model of the electrical properties of the spinal cord and surrounding tissues was used in order to predict which fibers in the spinal cord would be excited by epidural stimulation. In 1986, Holsteimer et. al. started a study using a similar approach to analyze the effects of various geometric parameters and to relate them to clinical data[9].

[7] Swiontek T J., Sances A., Larson S J., et. al., "Spinal cord implant studies", IEEE Trans Biomed Eng. 1976, BME-23: 307-312.
[8] Coburn B., "Electrical stimulation of the spinal cord: Two-dimensional finite element analysis with particular reference to epidural electrodes", Med Biol Eng Comp 1980, 18:573-584. Sin WK., Coburn B., "Electrical stimulation of the spinal cord: A further analysis relating to anatomical factors and tissue properties", Med Biol Eng Comp 1983; 21:264-269. Coburn B., Sin W K., "A theoretical study of epidural electrical stimulation of the spinal cord. Part I. Finite element analysis of stimulus fields", IEEE Trans Biomed Eng 1985; BME-32:971-977. Coburn B., "A theoretical study of epidural electrical stimulation of the spinal cord. Part II. Effects on long myelinated fibers", IEEE Trans Biomed Eng 1985; BME-32:978-986.
[9] Holsheimer J., Struijk J J., "Electrode combination and specificity in spinal cord stimulation", Proc 9$^{th}$ a Int Symp Advances in External Control of Human Extremities, Dubrovnik, 1987, pp. 393-404. Holsheimer J., Struijk J J., "Analysis of spinal cord stimulation. 1. Field potentials calculated for a homogeneous medium; in Walling a W., Boom H B K, de Vries J. (eds): *Electrophysiological Kinesilogy*, Amsterdam, excerpta Medica Congress Series, 1988, Vol. 804, pp. 95-98. Struijk J J., Holsheimer J., Van Veen B K, et. al., "Analysis of spinal cord stimulation. 11. Simulation of field potentials in an inhomogeneous medium", in Walling a W., Boom H B K., de Vries J. (eds): *Electrophysiological Kinesiology*, Amesterdam, Excerpta Medica Congress Series, 1988, Vol. 804, pp. 99-102. Holsheimer J., Struijk J J, "Improvement of methods in spinal cord stimulation", Int J Rehab Res 1989, 11:409-410. Struijk J J., Holsheimer J., Van Veen BK., Boom H B K., "Epidural spinal cord stimulation: Calculation of field potentials with special reference to dorsal column nerve fibers", IEEE Trans Biomed Eng 1991; BME-38:104-110.

It is important to note that the described process remains completely manual and incremental, and may not lead to the 3 or 4 best programs for the patient. That is precisely what I would like to automatically obtain when one cannot try all possible options. In the cases that are not covered by "rules", when one uses a trial-and-error method, there are too many different options. Simply trying them all is not possible. Therefore, one requires intelligent methods for generating the best SCS programs.

Existing SCS devices have demonstrated several deficiencies, especially in terms of cost, convenience, and efficiency:

a) First, it takes too long to determine the optimal set of stimuli to apply to the patient in relation to the large number of possible combinations.

b) Second, each patient is required to visit a physician several times to adjust the system, which can become prohibitively expensive.

c) Third, the selection of the appropriate program and the control of the electric signal parameters—frequency, amplitude, and pulse width—must be done manually by the patient.

In summary, existing SCS devices are not intelligent, they are not self-learning, and they do not provide automatic feedback. Existing SCS devices are not intelligent, self-learning, or automatic because none of the existing technologies which SCS devices utilize are advanced enough.

In fact, there are not even any new patents which purport or claim to automatically adjust a patient's pain treatment levels based upon automatic feedback from actual, specified, physical and/or physiological patient parameters.

Based upon a recent search, we found several related works on neural stimulation for pain control. Most of the patents proposed a straightforward solution without incorporating any automatic feedback loop between the patient and the system.

U.S. Pat. Nos. 4,233,986 and 4,735,204 describe a conventional neural stimulator for pain control where a practitioner, based on patient feedback, manually controls the strength of the signal applied to the electrodes.

U.S. Pat. No. 5,702,426 presents a method to automatically adjust the electrical signal parameters on implantable medical devices. This approach still does not contain any feedback from human physiological parameters as a result of the electrical stimulation.

U.S. Pat. No. 5,913,882 presents neural stimulation techniques to incorporate feedback to control the amplitude of the pulse generator to maintain a more uniform stimulation effect.

U.S. Pat. No. 6,909,917 presents a new method to determine a desired stimulation pattern applied to an electrode or a group of electrodes. The patient or physician uses a friendly user interface to program which group of electrodes will be targeted as well as the current waveform on each contract. Though this patent provides a method to efficiently program an SCS device via a graphical user interface to generate quality stimulation to the patient, there is no automatic detection of pain levels and there is no automatic generation of corresponding appropriate stimulation programs.

U.S. Pat. No. 6,622,048 presents a method to program an implanted SCS through the use of a computer. The computer is connected to the implant device in order to adjust the applied stimuli to each area of perceived pain. The patient or physician communicates with the computer to provide inputs for both the body's area of pain and the resulting area to be covered by the stimulation. The computer uses this information to quickly change the electrode configuration and to generate the appropriate stimulus parameters. This is primarily done by using a database that maps various electrode combinations to both the pain region and the region that is covered by the stimulation. This patent provides no feedback loop and adaptive behavior within the SCS system to enable the SCS system to automatically generate the best stimulation programs once pain is felt by the patient.

U.S. Pat. No. 6,871,099 is a small implantable stimulator that can be located near or within a region of the spinal cord where pain is sensed. This particular stimulator has at least two electrodes to provide the means for stimulating a nerve or tissue when desired. This small stimulator can also work as a closed loop using at least one sensor which will adjust the stimulation parameters based on the sensed coupling condition. This patent proposes a first step toward providing a closed-loop system. However, this invention does not provide true intelligence since it does not understand whether the patient feels pain or not, and, hence, it cannot automatically trigger stimulation with the most appropriate program. In addition, the stimulator is limited to coverage of a small region of the body. The use of this device is limited to stimulation of a single nerve, and, therefore, is incapable of providing patients with the broad spectrum and array of stimulation and pain relief afforded by a spinal cord stimulator system. Moreover, this invention would require several stimulators to be implanted to cover a larger region; hence, it requires much more complicated patient surgery.

U.S. Patent 20030153959 has been recently filed, in 2003. It describes a system based on current SCS technologies, providing automatic adjustment of stimulus output as a function of sensed coupling efficiency. This system is based on a sensor that measures the coupling efficiency of an electrical stimulation applied to neural tissue in order to automatically adjust the appropriate magnitude of stimulating current pulse to the patient. We consider this patent to be a preliminary system towards automatic control of pain.

Our system goes beyond this concept, as it is based on multiple sensors monitoring different aspects of the patient's pain status in order to automatically adjust the correct electric current pulses and find the best contact polarity on the leads in order to provide the patient with the best pain relief possible. One of the major advantages is that our system is capable of auto-configuring itself by learning how the patient will react based on applied stimuli. Our system actually creates an automatic feedback loop using a set of input sensors, analyzes the data (from the data fusion process), generates a diagnostic, and gradually adjusts the right stimulus being applied.

This referenced competitor system (U.S. Patent 20030153959) does not include a self-learning capability within the system to automatically adjust its stimuli. In addition, this competitor system cannot rapidly program the polarity of the electrode points. Moreover, this approach is significantly variant; as such, it does not threaten our patent application.

OBJECTS AND ADVANTAGES

Accordingly, several objects and advantages of my present invention are:

a) To provide intelligence and autonomy to SCS devices b) To provide SCS devices with self-learning capabilities—obviating the prevalent practice of basing "settings" on trial and error approaches and on patient "hunches."

c) To provide automation to SCS devices—obviating the need for time-consuming manual intervention.

d) To provide a feedback loop to SCS devices—supplying physicians and patients with much needed data in real-time.

e) To provide a classification of the patient's pain intensity—also referred to as "levels of discomfort."

There is a strong demand in the marketplace for an intelligent SCS system that can be easily personalized (automatically search for the best stimuli) for each patient. This intelligent system would automatically adjust electrical signals in relation to intensity of pain, but without continued human intervention after surgical insertion.

This invention is intended to considerably enhance existing (or future) SCS devices. Existing solutions or proposed patents still do not provide any intelligence, self-learning, or self-adaptation to analyze the patient's pain conditions and generate the most appropriate SCS program.

Another advantage is that this invention will greatly improve the patient's autonomy, reduce the number of clinical visits, and, hence, reduce medical costs. Most important, no prior art has proposed a self-contained system that is capable of self-adapting (without human intervention), and changing its internal parameters automatically.

The invention's novelty revolves around 5 main features:

a) the sensor fusion of the patient's measured physiological parameters;
b) the internal representation and classification of the different pain levels (or levels of discomfort) felt by the patient;
c) detecting when the patient is feeling pain without requiring any patient intervention
d) the system's capability to continuously learn and re-configure itself vis-a-vis the patient
e) the automatic selection of previously used SCS programs—or the generation of new SCS programs—to provide pain relief with maximum coverage and minimum side effects.

It is important to note that this invention is intended to considerably enhance existing (or future) SCS devices and that today such SCS devices are used primarily for chronic pain management by targeting electrical stimulation of the spinal cord.

However, SCS devices can also be used for treating chronic intractable angina (for which SCS therapy is used in Europe, but not used much in the USA), peripheral vascular disease, obesity, and depression. My invention can also be utilized as an "add-on" system to enhance SCS devices used for treating these above-mentioned indications.

My invention can also be utilized to enhance electrical stimulation devices (other than those that target the spinal cord) that target the treatment of the following additional niche markets:

Deep brain stimulation (for treating essential tremor and Parkinson's disease)
Vagus nerve stimulation (for treating epilepsy and depression)
Sacral nerve stimulation (for treating urge incontinence and pelvic pain)
Peripheral nerve stimulation (for treating chronic pain, occipital neuralgia, and chronic headache)
Transcutaneous Electrical Neural Stimulators (TENS) for pain.

In addition, my invention can be utilized to enhance the convenience and effectiveness of other marketed pain management devices, including:

Morphine Pumps—which treat chronic pain and cancer pain
Intrathecal Pumps—which treat neuropathic pain and muscle spasms Further objects and advantages will become apparent from a consideration of the ensuing description and drawings.

SUMMARY

My invention is a self-adaptive system for the automatic detection and classification of the patient's level of discomfort, and the automatic generation of adequate SCS therapies (also called SCS programs). This invention is intended to considerably enhance the efficiency and effectiveness of existing (or future) spinal cord stimulator devices for chronic pain management.

The primary object of the present invention is to create a system that can be "added on" to existing or future SCS devices, but which will greatly improve the functionality, efficiency, clinical effectiveness, and cost effectiveness of these devices, since it will enable such SCS devices to automatically detect discomfort, to automatically generate SCS therapies, and to adapt itself to changes in the patient, without any human (patient or physician) intervention.

DRAWINGS

Figures

FIG. 1—System Context Overview. This figure shows how my invention (the proposed system) fits into an overall SCS device system. My proposed system is an add-on to existing or future SCS devices, and will be incorporated into the implantable pulse generator (IPG) part of such IPG-type SCS devices.

FIG. 2—System Block Diagram. This figure is a detailed diagram of my invention. It shows how the Execution Unit (EU) and the Supervision Unit (SU) interact. It shows the functionality of all the Execution Unit's sub-units: the Adaptation and Filtering Unit (AFU), the Sensor Fusion Unit (SFU), the Lookup Table Unit (LTU), and the Program Generation Unit (PGU). And, it shows how the patient, system expert, the implantable pulse generator (IPG), and perception nerve sensors interact with the system.

FIG. 3—The Kohonen Neural Network. This figure shows the structure of a Kohonen self-organizing map containing 2 layers: i) an input layer where each neuron will be connected to a sensor signal after being processed by the Adaptation and Filtering Unit (AFU), and ii) an output layer that conveys the topographic representation (or 2D map) of the patient's level of discomfort. Only one output neuron will be activated at a time. Each output neuron characterizes a level of discomfort.

FIG. 4—Scenarios of Steering Current. This figure illustrates examples of how the current is traversing between 2 leads, circulating between the anode (−) to the cathode (+) contacts.

FIG. 5—Lead Placement Scenario. This figure shows an example of how the leads need to be placed along the spinal cord to cover a particular region of the body (in this case the lower body). It also shows the relation between the contacts on the lead and the body sub-regions to stimulate.

FIG. 6—Chromosome Representation. This figure shows the data representation that is used to describe an SCS program in the context of a Genetic Algorithm. Each chromosome is composed of genes. Each gene is either a "guarded cathode" or "split anode" element. Possible values of these genes can be found in FIG. 11.

FIG. 7—Crossover Example. This figure shows an example of a crossover operation between 2 chromosomes (or 2 contact combinations).

FIG. 8—Mutation Example. This figure shows an example of a mutation operation between 2 chromosomes.

FIG. 9—Examples of Undesirable Combinations. This figure shows examples of contact combinations that will not provide any stimulation in a particular region of the body since no current will traverse from one lead to another. At least one anode and one cathode are needed to deliver current through the leads.

FIG. 10—Genetic Algorithm for Automatic SCS Program Generation. This figure shows the template of the genetic algorithm to generate new SCS programs.

FIG. 11—Gene Pool. This figure shows all the "guarded cathode" (group of 3 contacts) and "split anode" (group of 2 contacts) combinations that will be used by the Genetic Algorithm to generate new SCS programs. Genes in a chromosome can only be assigned one of those values.

DETAILED DESCRIPTION

FIG. 1—Preferred Embodiment

FIG. 1 shows the proposed invention in a system context overview. My invention, as described herein, is labeled the "proposed system" or "proposed invention." The proposed invention represents a process, or method, of generating electrical "programs" or "therapies" for patients who utilize spinal cord stimulation (SCS) devices to control pain in various parts of their bodies. The proposed invention is, thus, one component or module within an SCS device. My invention is incorporated, as an add-on, into current or future implantable spinal cord stimulator (SCS) devices that treat pain. My invention will enhance the capabilities of SCS devices available on the market. The proposed invention, in the preferred embodiment, aims at being integrated within the implantable pulse generator (IPG) of a typical SCS system (see FIG. 1).

The proposed invention is comprised of:
- a) at least one sensor to sense at least one physiological patient parameter;
- b) at least one embedded system to carry out the operations of acquisition, fusion and classification, storage, generation, and self-adaptation. (All of these operations are described in detail in the next section, "Operation.");
- c) at least one interface from the sensor(s) to the lead(s); and
- d) at least one interface from the embedded system to at least one component of the implanted pulse generator (IPG) part of an SCS device.

The proposed invention is not intended to replace, in whole, existing or future SCS devices.

I must produce an External System Interface (labeled here in FIG. 1 "External System Interface") in order for my proposed system to interface with one or more existing or future SCS devices. However, specifications for such an External System Interface cannot be provided here, because in order to determine specifications, I would need proprietary information from the manufacturer of an existing (or future) SCS device. Such information, which I do not have in any case at this time, would not be available for publication due to its confidential nature.

Operation

FIGS. 2, 3, 4, 5, 6, 7, 8, 9, 10, 11—Preferred Embodiment

My invention is an intelligent, self-learning system that automatically auto-configures for each patient (current solutions are manually programmed by an expert, and need to be re-programmed or adjusted every month or so). It also provides an automatic feedback loop through its sensors, which measure and monitor patient parameters such as temperature, blood pressure, transcutaneous oxygen tension, heartbeat, sudomotor performance, vasomotor, sweat, skin conductance, electroencephalograph (EEG), and sensory nerve threshold sensors to monitor the body area for discomfort. If needed, any other type of sensors can be used with the proposed invention.

My invention incorporates intelligence (e.g. non-polynomial (NP) algorithms, neural networks, and genetic algorithms) in order to generate the most appropriate pain management configuration for each patient.

My invention represents a huge innovation because my system has automatic learning and feedback abilities, thus eliminating the need for manual patient feedback. In this manner, the patient can be treated much faster, resulting in fewer and shorter physician visits, greater patient autonomy and satisfaction, lower overall medical costs, and better clinical outcomes.

In the background section, I already introduced the main components of an SCS system and highlighted the limitations of current solutions. In summary, the fact that existing solutions need to be frequently reprogrammed by a pain specialist is one of the major drawbacks. This lack of autonomy results in frequent physician visits, higher medical costs, and less patient autonomy.

There are several factors that result in the SCS parameters (contact polarities, signal pulse width/frequency/amplitude) needing to be re-adjusted, including: (a) the leads placed along the spinal cord can accidentally move, or (b) The patient's discomfort perception threshold caused by the electrical stimulation can change over time. Pain specialists explain this behavior as being due to the non-usual feelings provided by the electrical stimulation, mostly happening in the early weeks after surgery. The patient can also get accustomed to the electrical stimulation.

Pain is a very subjective feeling and hence hard to quantify. However, pain generally causes a general arousal in the autonomic output (blood pressure, heart rate, sweat, skin conductance, temperature), which is mediated by an increase in epinephrine and nor-epinephrine hormones. Therefore, by taking measures of pulse rate, skin conductance, skin temperature, and blood pressure, it is possible to measure and quantify the physiological arousal caused by experiencing pain.

In addition, since pain is perceived within the brain, it is also possible to measure brain activity using an electroencephalograph (EEG) in order to determine the extent to which the patient is experiencing pain. It has been shown that subjective reports of pain do correlate with electrical changes that show up as peaks in EEG recordings.

Other parameters are also useful to evaluate a patient's discomfort level, such as vasomotor, sudomotor, and transcutaneous oxygen tension.

Muscle tension measured via electromyograph (EMG) can also be associated with painful conditions such as headache and lower backache. EMG measures muscle tension or electrical activity in muscles, which is a sign of how tense they are. This is detectable with skin surface sensors. However, an EMG alone does not necessarily correlate to pain. It has to be combined with the other physiological parameters mentioned above.

The major novelty of this invention is its capability to learn, adapt, and self-configure its internal parameters and programs while monitoring the patient. By continuously monitoring and analyzing the patient's physiological parameters discussed above, one can determine at any time the patient's discomfort level (also called patient discomfort status). This process is called sensor fusion, as it involves the integration of data streams from disparate sensors to form a unique, consistent model that represents how the patient is feeling.

It is also important to mention that autonomic arousal can occur in the absence of pain. For example, anxiety, alcohol consumption, or miscellaneous infection will cause physiological changes such as an increase in the patient's pulse rate, not necessarily related to the intensity of pain being experienced. Therefore, the invention needs additional information for pain detection.

The invention also learns about the patient by registering in its internal memory the SCS programs being selected when the patient is experiencing pain. Thus, the combination of both the patient's discomfort status and the SCS programs activated creates an associative map that will assist the invention in pain detection and in the search for the best spinal cord stimulation program. In other words, the proposed system continuously establishes a history of the patient's pain activity by building a look-up table between the patient's various discomfort statuses or levels and the programs selected by the patient when pain is felt.

The best electrical stimulation is achieved when the entire zone of the body affected by pain (target region) is fully covered during the stimulation (i.e. the patient is not over or under stimulated) while minimizing stimulation on undesired regions, and a level of comfort is obtained. An optimal stimulation will lead to paraesthesia.

Typically, during the patient's visits, the spinal cord stimulator programs and parameters will be re-adjusted by the pain specialist (or system expert). The longer the system is used, the more data (patient discomfort statuses and programs) is acquired by the proposed system resulting in more system autonomy and less patient visits, until almost no visits will be needed.

The goal is to accumulate enough data to automatically detect when pain is felt, by mapping the input vector drawn from the sensors to a discomfort status stored in the system look-up table, and then applying the corresponding SCS program to the patient until pain relief is reached. If more then one program is stored, the proposed system activates them one after the other, and stops as soon as the sensor values (a.k.a. discomfort status) indicate that the level of discomfort is non-existent.

However, this approach assumes that the patient's reaction remains identical if the same SCS program is applied more than once. This is not always the case as we explained earlier in this section. Therefore, the proposed invention has the capability to adapt to those situations and generate new SCS programs to relieve the patient using an effective, controlled, investigative probing search and monitoring method. This is achieved by continuously monitoring the new values produced by the sensors in real time, thus creating a biofeedback effect.

The invention is to be incorporated inside the implantable pulse generator (IPG). The sensors are the inputs of the system. Different alternatives are proposed to get the physical data from the patient. For example, one can use a bracelet, or implanted sensors inside the patient or on the leads depending on which physical information needs to be measured. Vital parameters, namely, temperature, sweat, blood pressure, and skin conductance, can be measured from on-surface sensors using a bracelet.

Once these vital parameters are measured at regular intervals, they are compared with the values that have been stored inside the system from previous measures. As a result, the correlation between the actual data and the data stored previously helps the system to establish a diagnostic of the patient's status.

From there, the system matches the diagnostic to a set of corresponding stimulation programs that will be converted into electrical signals and sent to the spinal cord via the generator and the leads. The system will then acquire new sensor values as a result of the new stimulation. Again those values will be compared to the data in memory to indicate if an improvement of the patient has been detected. If no or minor improvement has been detected, the system will generate a new set of programs that are derived from the ones that have been sent initially. The system continues to gradually adapt its programs until the sensor measurements indicate pain recovery (i.e., when the temperature, sweat, skin conductance, are back to their normal range).

As shown in FIG. 2, the invention is divided into 2 major components: a Supervision Unit (SU) and an Execution Unit (EU). The execution unit includes an Adaptation and Filtering Unit (AFU), a Sensor Fusion Unit (SFU), a Lookup Table Unit (LTU), a Program Generation Unit (PGU), and a General Purpose Memory. The Execution Unit is also connected to an External System Interface (a unit interfacing the proposed invention with existing or future SCS devices), which is depicted in FIG. 1.

The Sensor Fusion Unit (SFU) is a smart acquisition interface. It measures the signals produced by the sensors and merges this data into a comprehensive representation of the patient's level of discomfort: the pain status. Even though it is hard to quantify pain, the Sensor Fusion Unit relies on the fact that pain causes a general increase in the patient's autonomic output compared to his (or her) baseline condition. Thus, the Sensor Fusion Unit analyzes how the physiological signals coming from the sensors correlate with one another. It is the combination of all the physiological parameters measured that allows the Sensor Fusion Unit to deliver the best diagnosis.

The Sensor Fusion Unit is absolutely not limited to the processing of only the sensors proposed herein. It can be easily re-configured to accept a larger selection of sensors if needed. Implanting the sensors at different locations of the patient's body can increase the complexity and duration of the surgical procedure. There are different scenarios to implant the sensors. The sensors can be either integrated inside the leads or placed on the SCS receiver, which is inserted in the patient's body. Another option would be to mount the sensors on any kind of apparatus that can easily be worn by the patient that would also enable monitoring of the patient's physiological parameters. Examples of such options would be a bracelet, worn on the wrist, a legband worn on the leg, a headband worn on the head, a necklace worn on the neck, or a waistband worn on the waist. Sensors signals can then be remotely transmitted to the invention.

The proposed invention includes a self-adaptive capability to acquire the desired knowledge in order to increase the patient's autonomy. Therefore, the Sensor Fusion Unit must be able to learn and generalize the gained knowledge from the physiological inputs. Artificial neural networks are powerful general-purpose tools that have been applied successfully to prediction, classification, and clustering problems. They are used in a variety of areas including medical diagnosis. The advantages of using a neural network as an implementation of the Sensor Fusion Unit include real time operation, adaptability to unstructured environments, parallel processing of sensor data, and fusion of multi-sensory information.

Since the patient's condition is somewhat unpredictable, there is no predefined training set or historical data available to teach the neural network about the problem it is supposed to solve. Some type of unsupervised learning and self-organizing capability is needed—which will modify its internal weights associated with each of the neural connections based on the characteristics of the input pattern only. Unsupervised learning does not need the intervention of a human operator to provide the desired outputs for the corresponding inputs.

For example, a popular type of unsupervised learning is competitive learning where neurons compete among themselves to be activated. Only one single output neuron is activated at any time. The self-organizing map is a type of competitive learning neural network. Kohonen introduced the concept of topographic map formation. He proposed a self-organizing system based upon a network of adaptive laterally interconnected neurons, where the spatial location of an output in the topographic map corresponds to a particular feature of its input pattern[10]. The goal is to discover some underlying structure of the input data. In my application, the Kohonen neural network allows me to project multi-dimensional points (i.e. input sensors x1, x2, . . . , xn connected to the input layers) to a multi-dimensional grid or array (also called the Kohonen layer), as shown in FIG. 3.

[10] T. Kohonen, Self-Organization and Associative Memory. Springer-Verlag, 1984. ISBN: 3540-12165-x Third edition 1989.

Each output neuron of the grid represents a status of the patient's discomfort. The size N*N of the Kohonen layer is determined by both the number of input sensors and the status level (discomfort level) that we would like to generate. However, due to hardware and power consumption limitations, the number of output neurons should be kept to a minimum. The Kohonen neural network does not contain any internal layer. The Sensor Fusion Unit receives its inputs from the Adaptation and Filtering Unit as a normalized input vector. It also receives its internal weight values and learning parameters such as the learning rate and the neighborhood function from the Supervision Unit.

The Kohonen learning algorithm involves an iterative process composed of 5 steps:

a) Weights $\omega i$ are initialized to small random numbers, close to 0; The initial learning rate $\alpha(t)$ and neighborhood function $\sigma(t)$ are also set. The learning rate is a value decreasing with time used by the learning algorithm to adjust the weights. Generally setting the learning rate to a larger value will cause the training to progress faster but could cause the network to never converge. The system needs some time to learn so that the Sensor Fusion Unit can acquire as much patient data as possible. Initial values between 0 and 1 (e.g. 0.4 or 0.5) will be provided.

b) Apply an input vector {x1, x2, . . . , x3) and select the "winner" output neuron. The winning neuron with index k corresponds to the weight wk which is the closest approximation of the current input vector x. We use the Euclidian distance to determine the smallest distance dj between input xi and the weight $\omega ij$ (for i=1, . . . , n and j=1, . . . , m)

$$\|x-\omega k\| = \min\ dj = \|xi-\omega ij\| = [\Sigma(xi-\omega ij)^2]^{1/2}$$

c) Next, the weights of the winning neuron and its neighbors are modified using the following training rule: $\omega ij(t+1)=\omega ij(t)+\alpha(t)*h(i,k)*(xi(t)-\omega ij(t))$ where h(i, k) is a decreasing function of the grid distance between units i and k such that h(k, k)=1 and falls off with the distance |i-k| between unit i and the winner neuron k in the output layer. Thus, the "winner" output neuron and its closer neighbors have their weights updated appreciably. Neurons located far away from the winner have their weights that do not change significantly. A Gaussian function can be used for this matter:

$H(i, k)=\exp[-0.5*((i-k)/\sigma(t))^2]$. $\sigma(t)$ is the neighborhood radius also decreasing with time.

d) Decrease the value of $\alpha(t)$ and reduce $\sigma(t)$.

e) Repeat steps 2 through 4 until the change in weight value converges or is less than a pre-specified threshold, or a maximum number of iterations is matched.

The learning rate and neighborhood radius are controlled by the Supervision Unit. The Supervision Unit is also in charge of updating the weights as long as the Sensor Fusion Unit has not converged to a point where enough physiological measures have been gathered from the patient. During the learning phase (training mode active), the objective is to provide good coverage for the patient's discomfort. As a result, when a new set of measures is sampled, it is easily classified and mapped onto an output neuron of the Kohonen map. Each output neuron represents a class or cluster of measures, which in turn corresponds to a patient's possible condition. For instance, one neuron corresponds to a stable condition when no pain is felt. Another neuron, when activated, will indicate that the level of discomfort is high. Another neuron, when activated, may indicate a mild level of discomfort.

The Sensor Fusion Unit has 3 modes: a standby mode, a training mode, and a forward processing mode. The standby mode is mostly used for power saving. During the forward processing mode, the sensor input signals are sampled at regular intervals and processed by the Sensor Fusion Unit to determine the patient's status (a.k.a. the "winner" neuron). For both the training and forward processing modes, input data are processed at a throughput defined by the pain specialist or system expert. The Supervision Unit triggers an internal timer, which sends a data_ready event to the Sensor Fusion Unit for each timing interval programmed. For example, the Sensor Fusion Unit can be programmed to process the sensor data every minute, 10 minutes, 30 minutes or every hour.

The Adaptation and Filtering Unit (AFU) is the interface between the array of sensors and the Sensor Fusion Unit. Its function is to prepare the data for the Sensor Fusion Unit. The signals generated by the sensors can be somewhat noisy, and hence must be filtered to obtain clean signals with smooth variations. A low-pass filter can be used to filter out undesirable spikes. One restriction of the Kohonen network is that it must have its inputs normalized as the signals variation should be between −1 and 1. This normalization is first achieved by calculating the length of the input vector. This is done by computing the square root of the sum of squares of all signals x1 as follow: $[x1^2+x2^2+x3^2+ \ldots +xn^2]^{1/2}$. Each filtered input signal is multiplied by the normalization factor $1/[x1^2+x2^2+x3^2+ \ldots +xn^2]^{1/2}$.

Same as for the Sensor Fusion Unit, the input data are sampled at regular intervals. The sampling signal sampling_clock is generated by the Supervision Unit. The Adaptation and Filtering Unit also has a standby mode that can be activated by the Supervision Unit.

The Lookup Table Unit (LTU) is the mechanism that monitors which SCS programs have been selected by the patient, and stores this information in memory. Once the proposed invention has accumulated enough information about the patient, we need a mechanism to monitor which SCS programs have been selected by the patient, and we must be able to store those in memory. Since those programs are triggered by the patient whenever pain is felt, it is logical to also store the corresponding discomfort status generated by the Sensor Fusion Unit. The programs being stored are a combination of contact polarities on the lead, and signal characteristics (pulse width, amplitude, and frequency). A discomfort status could be associated more than one program, as the patient might adjust some of the parameters (primarily the voltage amplitude) if needed. At the same time, a discomfort status stored in the Lookup Table Unit that has no corresponding program could potentially indicate a favorable condition for the patient. In this case, no program will need to be triggered by the proposed invention during the forward processing mode.

The invention utilizes this concept to observe the patient's level of discomfort and automatically decides which SCS program to launch. It also determines when to stop the spinal cord stimulation as soon as a status indicating that the patient is relieved is generated by the Sensor Fusion Unit. The patient can manually stop the stimulation at any time during the process. The patient can also adjust the parameters such as the signal amplitude. If the patient feels better, he or she can request this new variation of program to be saved in the Lookup Table Unit (signal validate_scs_prg activated).

The discomfort status stored in the lookup table is the searching criteria (or map key). The Lookup Table Unit also stores the number of times a program has been activated, and the number of times it has been used with optimal effect by the patient. This is done so that the Lookup Table Unit can maintain an ordered list of programs for each discomfort status, from the most relevant program to the least. As a result, the first program on the list will have the highest priority and will be launched first. If no improvement is detected, the second program will be applied, and so on.

The Supervision Unit detects if the next program on the list needs to be started by monitoring the discomfort status coming from the Sensor Fusion Unit. A program will be tested for few seconds. If no relief has been reached, the Supervision Unit sends a signal run_next_program to the Lookup Table Unit to request the next program on the list. The memory content of the Lookup Table Unit can be entirely cleared by the Supervision Unit if needed. If a program is rarely used or has not been effective, then it can be erased from the memory. Due to memory capacity restrictions, the number of programs that can be stored at any one time for each discomfort status should be limited.

The Program Generation Unit (PGU) is the module that generates the optimal set of programs for pain relief. Once well trained, the proposed system has gathered enough data about the patient, including: a) a set of statuses characterizing the patient's levels of discomfort; and b) a list of SCS programs that the patient frequently selects when experiencing pain. The system is now capable of working in an autonomous fashion. In a best-case scenario, the system detects that the patient is feeling pain, and finds at least one program from the Lookup Table Unit to deliver an optimal stimulation. In this case, the Program Generation Unit is put in bypass mode by the Supervision Unit so that the SCS program coming from the Lookup Table Unit is directly transmitted to the unit that interfaces with the receiver within the spinal cord stimulator. As proposed in the previous section, each program is activated for several seconds to allow a reaction of the autonomic output, and hence a change of the patient's level of discomfort indicating that the pain level is decreasing.

However, the scenario where at least one of the SCS programs stored in the Lookup Table Unit is able to reduce the level of pain and achieve paraesthesia does not always happen. With current SCS solutions, the patient has to make an appointment with his (or her) pain specialist in order to get his system reprogrammed. With this invention, the number of patient visits for this matter will be reduced to a strict minimum as the Program Generation Unit's functionality is to automatically generate new programs for pain relief. In other words, the Program Generation Unit is capable of generating a new combination of electrode polarities, and pulse width/amplitude/frequency that will provide the paraesthesia effect.

In case the Program Generation Unit is not able to find a single program that covers the entire target region of the body, it will preferably generate a succession of programs, each of them covering a particular zone of the target region. These programs will be called sequentially in a cyclic fashion.

Typically, each lead can have up to 8 contact points (or electrodes). Since there are 3 values per electrode: positive (anode), negative (cathode), and zero, the total number of combinations can vary between $3^8=6,561$ for a 4 contact lead to $3^{16}=43,046,721$ for an 8 contact lead. We cannot try all the possibilities. We need to define an approach that will generate a limited numbers of programs to try on the patient for a few seconds until the reaction of the electrical stimulation results in a change of the physiological parameters being measured.

The leads are placed along the spinal cord at a specific location that covers the region of the where pain is felt as follows:

Neck→C2-C3

Shoulder→C4

Arms/hands/fingers→C4-C5

Low back, buttock, below beltline→T9-T10

Legs→T10-T11

Below the knee→T11-T12

Foot→T12-L1

The stimulation coverage greatly depends on how the leads are placed on both sides of the spinal cord. A common placement is to place one lead in the middle to get a longitudinal coverage, whereas the second lead is placed slightly lower on the right hand side, to cover the transverse part of the body region. The electric current is then steered from the anodes of one lead to the cathodes of the other lead, allowing the generation of an electrical field to suppress the signals going from the brain to the body and vice versa. FIG. 4 presents different steering current scenarios. The combination of positive and negative configurations on 3 adjacent longitudinal or transversal electrodes is called "guarded cathode". The combination of 2 electrodes is called "split anode". We will use these elements as a grouping factor in the formulation and representation of the problem to be solved—namely, finding the best SCS program to achieve optimal pain relief. Moreover, each "guarded cathode" and "split anode" group target the stimulation of a specific zone of the body. For example, as shown in FIG. 5, the leads are placed between T9-T10 and T12-L1 to cover the hips, left and right legs, and feet. Electrodes 1, 2, 3 and 9, 10, 11 are used to stimulate the hips, electrodes 4, 5, 6 and 12, 13, 14 covers the legs and knee, whereas electrodes 7, 8 and 15, 16 are used to stimulate the region of the feet.

Since we are dealing with a vast solution space, we would like to use a genetic algorithm (GA) to find a set of solutions that will work for the patient. A GA is a general-purpose search algorithm based upon the principle of evolution observed in nature[11]. A GA combines selection, crossover, and mutation with the goal of finding the best solution to the problem. This crossover-mutation-selection process favors the generation of better solutions from one evolution to another. This is done by selecting the best solutions and throwing away the worst ones.

[11] L. Davis, Handbook of Genetic Algorithms. Van Nostrand Reinhold, 1991.

In order to use a GA efficiently, we must represent a solution to the problem as a chromosome. Starting from an initial population set (chromosomes), the GA applies genetic operators such as mutation, crossover, and selection in order to find the best chromosome(s). There are 3 important items to define: (a) definition and implementation of the chromosomal representation, (b) definition and implementation of the genetic operators, and (c) definition of the fitness function.

Genetic representation will now be discussed. Each chromosome of the population represents one possible program combination. As shown in FIG. 6, the genes A, B, C, D, E, and F, which compose the chromosome, represent a group of 2 or 3 contact points. FIG. 7 shows the partition of a chromosome for an 8 contact lead. Gene A represents contacts 1 to 3 on lead 1. Gene B represents contacts 4 to 6 on lead 1. Gene C represents contacts 7 and 8 on lead 1. Gene D represents contacts 9 to 11 on lead 2. Gene E represents contacts 12 to 14 on lead 2. Finally, gene F represents contacts 15 and 16 on lead 2.

In order to express that genes can be substituted by a different one, we introduce a table of all possible combinations for "guarded cathode" and split anode" type of genes (see FIG. 11). For a lead with only 4 contacts, the chromosome representation is identical as it is for an 8 contact lead, although it is split in 2 "split anode" genes. At the beginning, the initial population contains the list of chromosomes coming from the preset programs stored in the Lookup Table Unit. Those programs will be mixed with a random list of chromosomes built from the gene pool table (see FIG. 11). In other words, the list of programs that the patient has used efficiently in the past will be altered by the GA to produce a better solution. Even though the list of programs that the patient has used efficiently in the past will be randomly altered by the GA, this process is proven to systematically result in producing better—in fact, optimal—solutions.

Genetic operators will now be discussed. The crossover operator selects 2 chromosomes (parents) among the fittest ones in the population, then combines them to produce a new chromosome (offspring). The idea is that the new chromosome may be better than both parents if it takes the best features from each parent. Our GA uses the uniform crossover approach that decides which genes from each parent will be selected to generate the offspring chromosomes. At each gene position, the probability of a gene being interchanged is $0<=p<=0.5$. This factor is also known as the mixing ratio from the parental chromosomes. FIG. 7 presents an example of gene crossover.

The mutation operator alters one or more gene values in an offspring chromosome from its initial value. This operator selects a point position according to a random value, and substitutes the gene randomly with another one from the gene pool in FIG. 11. We use a random value not exceeding 30%. FIG. 8 gives an example of mutation. Generally, the goal of the mutation function is to prevent the population from stagnating at any local optima.

The selection operator favors chromosomes of higher fitness to become the co-founders of the next population generation. Proportional selection (also known as "tournament selection") is used in this GA. The probability of a chromosome to be selected depends on its fitness. This method also allows even chromosomes with an inferior fitness value to be chosen. For example, we would rather select a program that only stimulates a sub-region of the body with good results, rather than picking a program that covers the entire region without properly providing relief to the patient.

The termination of the algorithm is achieved in 2 ways: (i) after a specified max number of iterations (or evolutions) defined by the system expert; (ii) as soon as a program or a list of sub-programs that match the fitness requirement has been found. We denote a sub-program to be a solution that does not entirely cover the target region. Instead, it only covers a partial area of the pain region, but with great results. The idea is to find a list of programs that could potentially cover each specific part of the target region (e.g. hip, foot, leg, knees) so that they can be called up by the system one after the other in a cyclic fashion.

The fitness function is a crucial element of the GA for the transmission of the gene information of a chromosome to the next generation. The selection operator uses this function to choose which chromosome will be elected to survive ("survival of the fittest"). We now present suitable fitness functions for the optimal relief of pain.

I now discuss how the system chooses the program(s) that provide the patient with optimal pain relief and coverage (or paraesthesia). We want to select a program that covers the target region of the body while minimizing the stimulation on undesired regions. In a successful stimulation, the patient feels tingling in the back (posterior), or back/front, but never in the front only (anterior). When a program retained by the selection operator is tested on the patient, the starting values of the pulse width, amplitude, and frequency of the electrical signals sent through the spinal cord are set as follow: a) For cervical, pulse width=50-250 ms; b) for thoracic, pulse width=150-500 ms. In both cases, the pulse rate (or frequency) can vary among patients from 30 seconds to 80 seconds and sometimes can reach 250 seconds. Both the frequency and pulse width are adjusted once by the pain specialist during the first visit. Under normal circumstances, the frequency and pulse width should remain constant. In most cases, a pulse width of 200 ms or 210 ms is programmed. The signal amplitude (or pulse amplitude) may vary between 0.1 volt and several volts. The amplitude depends on the distance between the epidural electrode and the dorsal columns in the spinal cord. The amplitude can be increased progressively, starting from the smallest value until the patient feels the effect of the stimulation. In order to optimize runtime and search efficiency, a few preset amplitude values can be programmed in the system.

I now propose an automatic way to determine where exactly the stimulation is felt by the patient, and especially when to stop increasing the signal amplitude: namely: internal or surface sensors placed at strategic locations on the body (e.g. arms, legs, beltline) can measure the sensory nerve threshold to indicate where the stimulation is felt, and more important if the perception is strong (i.e., need to decrease the signal amplitude) or too weak (need to increase the signal amplitude). The Program Generation Unit will immediately stop adjusting the parameters when the effect of the stimulation is optimal on the desired target region, and minimized on the regions we don't want to stimulate.

Basically, spinal cord stimulation raises the sensory nervous threshold. Before hand, the sensory perception threshold and the discomfort threshold are measured for each zone of the body. These values are a constant to the system and are different for each patient. The sensory perception threshold is the level obtained when the patient feels the stimulation. The discomfort threshold is the upper limit that should not be reached. It is the value when the stimulation is too strong, causing discomfort or pain to the patient. In between these two limits, the comfort threshold is also measured. It represents the optimal stimulation leading to paraesthesia. The comfort threshold is greater or equal than the perception threshold, but does not exceed the discomfort threshold.

We now formalize the problem to solve, which is how to tune or adjust the system parameters to obtain paraesthesia. We denote by $z1, z2, \ldots, zn$ the different values measures by the sensors on the target zones of the body, and $u1, u2, \ldots, um$ the values measured on the undesired zones. We also define a list of coefficients (or weights) $a1, a2, \ldots, an$ and $b1, b2, \ldots, bm$ that characterize a cost factor representing the strength of the stimulation on each of these zones. Those coefficients are inversely proportional to the strength of the stimulation on a particular region. The lower the coefficient, the stronger the stimulation should be at the corresponding region. If the coefficient value is high, then we need to reduce the stimulation on the corresponding region. This is explained by the fact that the patient might not feel the same degree of pain on all the target regions of the body. Thus, the stimulation needs to be stronger on certain zones, and weaker, or minimized on others. Ideally, it should be null on all the undesired zones, resulting in high coefficient values b1 to bm. The problem can easily be formulated using 2 linear equations:

total_comfort=$\Sigma ai*zi$; for $i=1$ to $n$ total_discomfort=$\Sigma bj*zm$; for $j=1$ to m Ideally, total_discomfort should be null (i.e. no undesired zone being stimulated), and total_comfort as close as possible to the optimal comfort value obtained at paraesthesia. The optimal comfort value is equal to optimal_comfort=$\Sigma$comfort_threshold(zi) for i=1 to n. The coefficients ai and bj are determined by the pain specialist by experiments, during the patient's initial visits. They are programmed within the Program Generation Unit. They can be adjusted if necessary. Each time a program is being tested on the patient, both values total_comfort and total_discomfort are computed and respectively compared to optimal_comfort and zero. Programs that generate a high total_discomfort value—or a total_comfort value that is too small—are eliminated. Additional constraints can be added to the Program Generation Unit to measure the effect (comfort or discomfort values) on one or several regions of the body.

Another method (alternative embodiment to the proposed invention) of obtaining quick feedback from the stimulation is to use a human-machine interface (e.g. LCD screen, notepad, joystick, keyboard, mouse, etc. . . . ) that communicates data remotely to the Program Generation Unit. This method is called a computer-based pain drawing approach[12]. The interface screen contains a representation of the patient's body. The patient uses an electronic pen to highlight the areas where stimulation is felt, and using a number between −10 and 10, the strength of the stimulation. A positive number would mean that the stimulation is too strong and needs to be reduced, whereas a negative value would signify that the stimulation is too low. Zero indicates that either the stimulation is perfect, or that the patient does not feel any tingling (which is wanted on undesired zones).

[12] North R B, Nigrin D J, Fowler K R, et al: Automated 'pain drawing' analysis by computer-controlled, patient-interactive neurological stimulation system. Pain 50:51-57, 1992.

For impaired people, another option would be to transmit the feedback of the stimulation on the different zones of the body by voice. In this case, a speech recognition algorithm is implemented in the Program Generation Unit. This, as well, is an alternative embodiment to the proposed invention.

I now discuss how to eliminate undesired solutions. Due to the randomness of the Genetic Algorithm (GA), several chromosomes that will not provide any kind of relief to the patient will be generated. For example, when the legs need to be stimulated, we expect genes B and E to contain a value that will steer current, with at least one anode and one cathode selected. Before even testing the solutions on the patient, a simple check is performed to filter out those chromosomes. FIG. 9 shows examples of genes that could potentially be rejected.

The Genetic Algorithm for the automatic selection of SCS programs is presented in FIG. 10. This algorithm naturally follows the template of a typical Genetic Algorithm.

Once the appropriate polarity combinations and signal amplitude/pulse width/frequency are found, they are sent to the Supervision Unit (SU) in order to be stored to the Lookup Table Unit. It is possible to generate a group of programs that partially cover a region of the body. Those programs will also be stored in the Lookup Table Unit. They will be encapsulated in a macro-program so that they can be sent sequentially to the SCS implantable pulse generator (IPG) in order to cover the entire discomfort region of the body.

I now discuss how to minimize power consumption. Since the system is incorporated into a portable device carried by the patient, power consumption is a major factor that must be considered in order to optimize the life of the battery. The selection process must choose the programs that will minimize the amount of current being steered. The energy consumed is directly related to the number of anodes and cathodes on both leads, as well as the signal amplitude. An empirical formula can be utilized to select or reject a program:

Energy~amplitude*num_anodes_lead1*num_cathodes_lead2+ num_anodes_lead2*num_cathodes_lead1

The Supervision Unit (SU) controls the processing of the data through the Execution Unit. Since the proposed system has different functioning modes, the Supervision Unit also controls how each module of the Execution Unit operates. Each module in the Execution Unit (i.e., the Adaptation and Filtering Unit, Sensor Fusion Unit, Lookup Table Unit, and Program Generation Unit) knows in which mode to operate by scanning their mode signal sent by the Supervision Unit: these are, respectively, SFU_mode, LTU_mode, and PGU_mode.

The standby mode can either be activated by the patient (for example at night time), or by the Supervision Unit when a period of inactivity has been detected. This happens when the status generated by the Sensor Fusion Unit has been stable (no discomfort level) for a certain period of time. The standby mode is important to save power in order to increase the battery life of the spinal cord stimulator.

During the training mode, the Adaptation and Filtering Unit, Sensor Fusion Unit and Lookup Table Unit modules are activated while the Program Generation Unit is put in standby mode. The input sensor signals are processed and normalized by the Adaptation and Filtering Unit at every active edge of the sample_clock signal generated by the Supervision Unit. This signal is derived from the clock signal coming from the clock global generator. Once the sensor data are ready to be processed, the Supervision Unit generates the signal data_ready to the Sensor Fusion Unit to indicate the start of the training mode. As explained earlier, the objective is to map the sensor measures onto a map (or 2 dimensional representation) of the patient's level of discomfort. In order to train the Sensor Fusion Unit, the Supervision Unit provides the required configuration parameters (see section 2). The training algorithm is software implemented within the Supervision Unit.

For the Supervision Unit (SU), the preferred embodiment is an embedded (software) program in a microcontroller. However, other types of implementation forms that can be used instead of this include, but are not limited to:

an application specific integrated circuit (ASIC)

a microprocessor a microcontroller an embedded (software) program in a microprocessor a system on a chip including analog components and interfaces a central unit with memory.

An entirely software-based module if the Supervision Unit is installed remotely (for example, on a central computer)

The Supervision Unit is responsible for reading and updating weight values. The Supervision Unit interacts with the general-purpose memory to retrieve and store temporary data during weight calculations. It should take the Sensor Fusion Unit a certain amount of time to be fully trained. However, even though the Sensor Fusion Unit may not be fully trained, its output signal—patient_discomfort_status—is still transmitted to the Lookup Table Unit and the Supervision Unit. Once an SCS program has been activated by the patient, this information is sent by the Supervision Unit to the Lookup Table Unit as well as the map_program_and_status signal to update the Lookup Table Unit's internal lookup table.

In the forward processing mode, the Adaptation and Filtering Unit, Sensor Fusion Unit and Lookup Table Unit remain activated whereas the Program Generation Unit can be placed in the bypass mode or new_program mode. In the bypass mode, the Program Generation Unit is transparent and the LTU_SCS program input data is forwarded to the generated_SCS program output program, which is sent to the implantable pulse generator (IPG). Although the weight values in the Sensor Fusion Unit should be well adjusted, the Supervision Unit can decide to re-compute the weights if needed. This can happen if the sensors deliver unexpected signal values, which might correspond to a new patient condition. When the run_program signal is sent, the Lookup Table Unit retrieves the first program in its list that corresponds to the patient's discomfort status generated by the Sensor Fusion Unit.

The Supervision Unit puts the Program Generation Unit in bypass mode and the SCS program is then transmitted to the spinal cord stimulator via the External System Interface. After few seconds, if no change of status has occurred, the Supervision Unit requests the Lookup Table Unit to launch the next program on the list. If no program has successfully relieved the patient or, if there are no more programs in the list, the signal no_program_available is activated. In this case, the Supervision Unit requests the Program Generation Unit to generate a new SCS program. This is done by assigning the value new_program_requested to the state variable pgu_mode, and activating the event mode_changed.

The Supervision Unit continuously monitors the state of the Program Generation Unit via the variable pgu_return_status which can take 3 values: searching_program, found_program, and no_program_found. The Supervision Unit also sets the maximum number of evolutions allowed during the program search. When a new program generated by the Sensor Fusion Unit provides a great stimulation, it is stored in the Lookup Table Unit for later use. In an extreme case, the Lookup Table Unit will not be able to find a program to relieve the patient. This can occur if the leads need to be re-positioned by surgery, or if the search requires too many loops exceeding the maximum number allowed. The variable pgu_return_status is then assigned the value no_program_found, indicating to the Supervision Unit that the spinal cord stimulation might need manual intervention to be re-programmed.

At any time during the training or forward processing modes, the patient can manually change the SCS parameters and validate these changes if they lead to relief (signal validate_scs_program activated). The Supervision Unit monitors this event and sends the appropriate signals and data to the Lookup Table Unit to take into account this modification. However, when the Program Generation Unit is searching for a new program, any parameter changes made by the patient will not be taken into account.

At any time the status of the system {training, standby, normal, need reprogramming, searching_program} are provided.

DESCRIPTION

Alternative Embodiments

This invention, as described herein, is integrated within the implantable pulse generator (IPG) component of an IPG-type of SCS device. However, my invention can also work equally well with radiofrequency (RF)-types of SCS devices, in which case my invention would be integrated within the transmitter part of an RF-type of SCS device. In the case of an RF-type of stimulator system, my proposed invention would be comprised of:

e) at least one sensor to sense at least one physiological patient parameter;

f) at least one embedded system to carry out the operations of acquisition, fusion and classification, storage, generation, and self-adaptation. (All of these operations are described in detail in the next section, "Operation.");

g) at least one interface from the sensor(s) to the lead(s); and h) at least one interface from the embedded system to at least one component of the transmitter part of an RF-type SCS device.

It is important to note that my invention will work equally well as an add-on component to both implantable pulse generator (IPG) spinal cord stimulator devices and radiofrequency (RF) spinal cord stimulator devices. An additional embodiment is that my invention could also be part of a centralized unit that will remotely monitor the patient's status and trigger an SCS program when needed.

In the above description, I have described an invention for a Self-Adaptive System for the Automatic Detection of Discomfort and the Automatic Generation of SCS Therapies for Chronic Pain Control. Using the specifications outlined in this description, any well-trained design engineer can create the system that I have described. As far as implementation of the overall system is concerned, the preferred embodiment described herein is a system on a chip, including analog interfaces (a mixed-mode analog-digital processor). However, the implementation can take many alternate forms (including, but not limited to):

a) it can be an application specific integrated circuit (ASIC)

b) it can be a microprocessor c) it can be a microcontroller with embedded software d) it can be a system on a chip including analog components and interfaces e) it can be a central unit with memory.

f) Or, it can be entirely software based, as long the "add-on" system is not fully integrated in the implantable pulse generator (for implantable SCS devices) or the transmitter (for radiofrequency SCS devices)

I claim rights to the system described herein, regardless of which of the above-mentioned implementation forms that it takes, since I can create this system using any of those forms.

Operation

Alternative Embodiment

For the sensor fusion component (called the Sensor Fusion Unit here), the invention uses a kohonen map. Other implementation alternatives could use any kind of unsupervised learning capability. In addition, supervised learning systems can also be utilized. These include, but are not limited to:

a) Fuzzy systems b) Conventional neural networks c) Neuro-fuzzy systems

If a fuzzy system or a neuro-fuzzy system is used, then it will require some pre-set training. With each sensor input, a membership function will be associated, and will need to be adjusted.

For the Program Generation Unit, the invention uses a genetic algorithm. However, other types of Non-Polynomial (NP) algorithms can be used instead of a genetic algorithm. These include, but are not limited to:

a) Linear programming techniques b) Tabu search c) Simulated annealing d) Dynamic programming algorithms For impaired people, another option would be to transmit the feedback of the stimulation on the different zones of the body by voice. In this case, a speech recognition algorithm is implemented in the Program Generation Unit. This, as well, is an alternative embodiment to the proposed invention.

The Supervision Unit (SU) described herein as the preferred embodiment is an embedded (software) program in a microcontroller. However, the implementation can take many forms other than this approach including, but not limited to:

a) it can be an application specific integrated circuit (ASIC)

b) it can be a microprocessor c) it can be a microcontroller d) it can be an embedded (software) program in a microprocessor e) it can be a system on a chip including analog components and interfaces f) it can be a central unit with memory g) or, it can be entirely software based.

CONCLUSIONS, RAMIFICATIONS, AND SCOPE

Accordingly the reader will see that my invention is a self-adaptive system to automatically detect and classify a patient's level(s) of discomfort, automatically generate the most appropriate electrical stimulation "program(s)" or "therapies" to relieve the patient's level(s) of discomfort, and automatically adapt itself to changes within the patient, all without any human (patient or physician) intervention. My invention is an "add-on" component that can be utilized within existing or future spinal cord stimulation devices.

My invention will work equally well as an add-on component to both implantable pulse generator (IPG) spinal cord stimulator devices and radiofrequency (RF) spinal cord stimulator devices. The invention, as described herein, is integrated within the implantable pulse generator part of an IPG-type of SCS device. However, my invention can also work equally well with radiofrequency (RF) SCS devices, in which case my invention would be integrated within the transmitter part of an RF SCS device.

My invention provides existing (or future) spinal cord stimulation devices with new, novel technologies which will greatly improve the functionality, efficiency, clinical effectiveness, and cost effectiveness of existing spinal cord stimulation devices, since it will enable such spinal cord stimulation devices to automatically detect discomfort, to automatically generate spinal cord stimulation "programs" or "therapies", and to adapt itself to changes in the patient, without any human (patient or physician) intervention.

My invention offers the following advantages over existing technologies:

It provides an unbiased, objective, effective, and repeatable method for collecting and classifying a patient's discomfort level(s) by utilizing a sensor fusion methodology to collect, measure, and classify multiple patient physiological parameters in real time.

It provides spinal cord stimulation devices with self-learning capabilities—obviating the prevalent practice of basing "settings" on trial and error approaches and on patient "hunches"—by utilizing patient physiological parameter data that has been collected, measured, and classified against historic patient "baseline" data and historic patient program choices.

It enables spinal cord stimulation devices to continuously learn and re-configure themselves vis-a-vis the patient.

It automatically detects when the patient is feeling pain without requiring any patient intervention It provides intelligence and automation to spinal cord stimulation devices—obviating the need for time-consuming manual intervention.

It provides a feedback loop to spinal cord stimulation devices—supplying physicians and patients with much needed data in real-time.

It enables spinal cord stimulation devices to automatically select and administer the most appropriate electrical stimulation programs or therapies to the patient. These programs can be programs that have previously been loaded into the system's memory or new programs which the system automatically generates It enables spinal cord stimulation devices to automatically "choose" the most appropriate program (i.e., that program which will provide the patient with maximum pain relief coverage and minimum side effects) for the patient at any given point in time.

While the above description contains many specificities, these should not be construed as limitations on the scope of the invention, but as exemplifications of the presently preferred embodiments thereof. Many other ramifications and variations are possible within the teachings of the invention.

For example, as far as implementation of the overall system is concerned, the preferred embodiment is a system on a chip, including analog interfaces (a mixed-mode analog-digital processor). However, the implementation can take many alternate forms (including, but not limited to):

it can be an application specific integrated circuit (ASIC)

it can be a microprocessor it can be a microcontroller with embedded software it can be a system on a chip composed mainly of analog interfaces it can be a central unit with memory.

Or, it can be entirely software based, as long the "add-on" system is not fully integrated in the implantable pulse generator (for implantable SCS devices) or the transmitter (for radiofrequency SCS devices)

Additionally, for the sensor fusion component (called the Sensor Fusion Unit here), the preferred embodiment uses a kohonen map. Other implementation alternatives could use any kind of unsupervised learning capability. In addition, supervised learning systems can also be utilized. These include, but are not limited to:

Fuzzy systems

Conventional neural networks

Neuro-fuzzy systems

If a fuzzy system or a neuro-fuzzy system is used, then it will require some pre-set training. With each sensor input, a membership function will be associated, and will need to be adjusted.

Additionally, for the Program Generation Unit (PGU), the preferred embodiment uses a genetic algorithm. However, other types of non-polynomial (NP) algorithms can be used instead of a genetic algorithm. These include, but are not limited to:

Linear programming techniques
Tabu search
Simulated annealing
Dynamic programming algorithms Additionally, for the Supervision Unit (SU), the preferred embodiment is an embedded (software) program in a microcontroller. However, other types of implementation forms that can be used instead of this include, but are not limited to:

an application specific integrated circuit (ASIC)
a microprocessor
a microcontroller
an embedded (software) program in a microprocessor
a system on a chip composed mainly of analog interfaces
a central unit with memory.
An entirely software-based module It is important to note that this invention is intended to considerably enhance existing (or future) SCS devices and that today such SCS devices are used primarily for chronic pain management by targeting electrical stimulation of the spinal cord.

However, SCS devices can also be used for treating chronic intractable angina (for which SCS therapy is used in Europe, but not used much in the USA), peripheral vascular disease, obesity, and depression. My invention can also be utilized as an "add-on" system to enhance SCS devices used for treating these above-mentioned indications.

My invention can also be utilized to enhance electrical stimulation devices (other than those that target the spinal cord) that target the treatment of the following additional niche markets:

Deep brain stimulation (for treating essential tremor and Parkinson's disease)
Vagus nerve stimulation (for treating epilepsy and depression)
Sacral nerve stimulation (for treating urge incontinence and pelvic pain)
Peripheral nerve stimulation (for treating chronic pain, occipital neuralgia, and chronic headache)
Transcutaneous Electrical Neural Stimulators (TENS) for pain.

In addition, my invention can be utilized to enhance the convenience and effectiveness of other marketed pain management devices, including:

Morphine Pumps—which treat chronic pain and cancer pain
Intrathecal Pumps—which treat neuropathic pain and muscle spasms Thus the scope of the invention should be determined by the appended claims and their legal equivalents, and not by the examples given.

I claim:

1. A method for treating a patient with chronic pain, the method comprising:
   providing signals to at least one lead implanted in a patient, the signals based on sets of stimulation parameters, the lead delivering the signals to nerves and tissue of the dorsolateral spinal cord of the patient;
   continuously monitoring patient parameters by recording sets of physiological measures from the patient;
   fusing a set of physiological measures by categorizing each set of physiological measures as one of a plurality of discrete discomfort levels produced by the chronic pain, wherein a discomfort level may include lack of pain;
   receiving sets of stimulation parameters selected by the patient;
   recording which sets of stimulation parameters are selected by the patient for each discomfort level;
   creating a table associating discomfort levels and selected sets of parameters; and
   automatically providing signals to the at least one lead based on the table,
   wherein the stimulation parameters consist of one or more parameters selected from the group consisting of: contact polarity, signal amplitude, pulse width, and frequency.

2. The method of claim 1, comprising, based on the set of physiological parameters, deciding in a computer processor whether or not to select a different one of the sets of stimulation parameters.

3. The method of claim 1, wherein the at least one implantable lead has a size and shape suitable for placement in the at least one dorsolateral area of the spine.

4. The method of claim 1, wherein the signals are provided by an implanted device connected to the at least one lead.

5. The method of claim 1, wherein the physiological parameters comprise qualitative perceptive changes felt by the patient.

6. The method of claim 1, wherein physiological parameters comprise one or more parameters selected from the group consisting of: temperature, blood pressure, transcutaneous oxygen tension, heartbeat, sudomotor performance, vasomotor, sweat level, skin conductance, sensory nerve threshold, electrcencephalograph (EEG), and stimulation location received from a human-machine interface.

7. The method of claim 1, wherein the sets of stimulation parameters are stored in a computer system, the method comprising automatically, in a computer processor, generating a set of stimulation parameters from existing stimulation parameters.

8. The method of claim 1, comprising:
   iteratively:
   generating a set of stimulation parameters;
   providing signals to at the least one lead based on sets of stimulation parameters;
   recording the level of pain relief; and
   for one or more parameters in the set of parameters, substituting the parameter with a randomly generated parameter;
   to find an optimal set of stimulation parameters.

9. The method of claim 1, comprising:
   determining two sets of stimulation parameters that are successful at reducing pain in a patient;
   combining elements from the two sets to create a new set stimulation parameters, wherein the elements are selected as being highly beneficial elements;
   applying signals to the at least one lead; and
   determining how successful the new set of stimulation parameters is at reducing pain.

10. A device for treating a patient with chronic pain, the device comprising:
    at least one lead implanted in a patient providing signals based on sets of stimulation parameters, the lead delivering the signals to nerves and tissue of the dorsolateral spinal cord of the patient; and a processor programmed to:
  continuously monitor patient parameters by recording sets of physiological measures from the patient;
  fuse a set of physiological measures by categorizing each set of physiological measures as one of a plurality of discrete discomfort levels produced by the chronic pain, wherein a discomfort level may include lack of pain;
  receive sets of stimulation parameters selected by the patient;
  record which sets of stimulation parameters are selected by the patient for each discomfort level and create a table associating discomfort levels and selected sets of parameters; and
  automatically provide signals to the at least one lead based on the table,
  wherein the stimulation parameters consist of one or more parameters selected from the group consisting of: contact polarity, signal amplitude, pulse width, and frequency.

11. The system of claim 10, wherein the processor is to, based on the set of physiological parameters, decide whether or not to select a different one of the sets of stimulation parameters.

12. The system of claim 10, wherein the at least one implantable lead has a size and shape suitable for placement in the at least one dorsolateral area of the spine.

13. The system of claim 10, wherein the signals are provided by an implanted device connected to the at least one lead.

14. The system of claim 10, wherein the physiological parameters comprise qualitative perceptive changes felt by the patient.

15. The system of claim 10, wherein physiological parameters comprise one or more parameters selected from the group consisting of: temperature, blood pressure, transcutaneous oxygen tension, heartbeat, sudomotor performance, vasomotor, sweat level, skin conductance, sensory nerve threshold, electroencephalograph (EEG), and stimulation location received from a human-machine interface.

16. The system of claim 10 wherein the processor is to automatically generate a set of stimulation parameters from existing stimulation parameters.

17. The system of claim 10, wherein the processor is to:
iteratively:
  generate a set of stimulation parameters;
  provide signals to at the least one lead based on sets of stimulation parameters;
  record the level of pain relief; and
  for one or more parameters in the set of parameters, substitute the parameter with a randomly generated parameter,
to find an optimal set of stimulation parameters.

18. The system of claim 10, wherein the processor is to:
determine two sets of stimulation parameters that are successful at reducing pain in a patient;
combine elements from the two sets to create a new set stimulation parameters, wherein the elements are selected as being highly beneficial elements;
apply signals to the at least one lead; and
determine how successful the new set of stimulation parameters is at reducing pain.

* * * * *